(12) United States Patent
Fabricius et al.

(10) Patent No.: US 10,835,677 B2
(45) Date of Patent: Nov. 17, 2020

(54) AUTO INJECTOR WITH CARTRIDGE RETENTION SYSTEM

(71) Applicant: Ascendis Pharma A/S, Hellerup (DK)

(72) Inventors: Paul Erik Fabricius, Holstebro (DK); Flemming Madsen, Aalborg SV (DK); Jan Olesen, Holstebro (DK)

(73) Assignee: Ascendis Pharma A/S, Hellerup (DK)

( * ) Notice: Subject to any disclaimer, the term of this patent is extended or adjusted under 35 U.S.C. 154(b) by 286 days.

(21) Appl. No.: 16/060,574

(22) PCT Filed: Dec. 29, 2016

(86) PCT No.: PCT/EP2016/082856
§ 371 (c)(1),
(2) Date: Jun. 8, 2018

(87) PCT Pub. No.: WO2017/114907
PCT Pub. Date: Jul. 6, 2017

(65) Prior Publication Data
US 2018/0361068 A1 Dec. 20, 2018

(30) Foreign Application Priority Data
Dec. 30, 2015 (EP) .................................... 15203132

(51) Int. Cl.
*A61M 5/24* (2006.01)
*A61M 5/20* (2006.01)

(52) U.S. Cl.
CPC ............ *A61M 5/2066* (2013.01); *A61M 5/20* (2013.01); *A61M 5/2033* (2013.01); *A61M 5/24* (2013.01);
(Continued)

(58) Field of Classification Search
CPC .. A61M 2005/2411; A61M 2005/2433; A61M 5/20; A61M 5/2066; A61M 5/24; A61M 5/2448
See application file for complete search history.

(56) References Cited

U.S. PATENT DOCUMENTS 9,173,995 B1  11/2015  Tucker et al.
2012/0283655 A1  11/2012  Plumptre et al.
(Continued)

FOREIGN PATENT DOCUMENTS

WO  WO 2014/166915 A1  10/2014

OTHER PUBLICATIONS

European Search Report for EP 15203137.3 dated Jul. 1, 2016.
International Search Report for PCT/EP2016/082856 dated Mar. 28, 2017.

Primary Examiner — Deanna K Hall
(74) Attorney, Agent, or Firm — Knobbe Martens Olson & Bear LLP

(57) ABSTRACT

An auto injector (4) for administering injection of a medicament from a cartridge (700) containing the medicament, the auto injector comprising: a cartridge receiver (300) with a cartridge receiver compartment (302) configured to receive a cartridge assembly (600) with at least one cartridge retention member (808) when inserted through a cartridge receiver opening (302) along a longitudinal axis; and an ejector (200) configured to support the cartridge assembly (600) by being suspended to move along the longitudinal direction and being spring-loaded in the direction opposite of the receiving direction. The cartridge receiver compartment (302) has a first section (310), at a first distance from the cartridge receiver opening (301), with inwardly extending first guide members (312) that extends over first guide member angles (314) and are spaced apart to form a passage (316) at passage angles (318) between the inward first guide (Continued)

members (312); wherein the inward first guide members (312) form a first bore (320) accepting the cartridge assembly (600) when inserted through the cartridge receiver opening (301). The cartridge receiver compartment (302) has a second section (330) with an annular shape, at a second distance from the cartridge receiver opening (301), and with second guide members (322) with first faces (324) that are inclined about a radial axis to the longitudinal axis and angularly arranged to extend at least partly over the passage angles (318) and the first guide member angles (314).

19 Claims, 10 Drawing Sheets

(52) U.S. Cl.
CPC ... *A61M 5/2448* (2013.01); *A61M 2005/2026* (2013.01); *A61M 2005/2411* (2013.01); *A61M 2005/2433* (2013.01); *A61M 2005/2481* (2013.01); *A61M 2005/2485* (2013.01)

(56) References Cited

U.S. PATENT DOCUMENTS

| | | |
|---|---|---|
| 2013/0211326 A1 | 8/2013 | Dasbach et al. |
| 2013/0211327 A1 | 8/2013 | Osman et al. |
| 2014/0142514 A1 | 5/2014 | Elahi et al. |
| 2014/0358093 A1 | 12/2014 | Soerensen et al. |

AUTO INJECTOR WITH CARTRIDGE RETENTION SYSTEM

CROSS REFERENCE TO RELATED APPLICATIONS

This application is a U.S. National Phase Application of PCT International Application Number PCT/EP2016/082856, filed on Dec. 29, 2016, designating the United States of America and published in the English language, which is an International Application of and claims the benefit of priority to European Patent Application No. 15203132.4, filed on Dec. 30, 2015, and European Patent Application No. 15203137.3, filed on Dec. 30, 2015. The disclosures of the above-referenced applications are hereby expressly incorporated by reference in their entireties.

The present invention generally relates to an auto-injector, which is an automatic or semi-automatic drug delivery device adapted to receive a drug filled cartridge and expel a dose therefrom.

In the disclosure of the present invention reference is mostly made to the treatment of Human Growth Hormone, HGH, however, this is only an exemplary use of the auto-injector.

The most common type of auto-injection devices adapted to receive a drug filled cartridge (also termed reservoir or container) and expel a dose therefrom are generally elongated e.g. pen-formed for being held in a user's one hand and utilizes a so-called cartridge holder adapted to receive and mount a cartridge in the device. Correspondingly, most pen-formed drug delivery devices comprise a generally cylindrical cartridge holder for receiving and holding a generally cylindrical drug-filled cartridge in a mounted position, the cartridge comprising a proximally facing and axially displaceable piston, and a main body with a housing in which a drug expelling mechanism is arranged, the mechanism comprising an axially displaceable piston rod adapted to engage the piston of a mounted cartridge to thereby expel a dose of drug from the cartridge. Between the cartridge holder and the main body coupling means is provided allowing a user to remove the cartridge holder from the main body and reattach it when a used cartridge has been exchanged with a new cartridge. The cartridge is inserted in the cartridge holder by axial movement through a proximal opening. Conventionally, the coupling means are in the form of a threaded connection or a bayonet coupling.

It is conventionally only insufficiently addressed that there is a need for devices that are easier and more intuitive to use.

RELATED PRIOR ART

US 2014/358093 and in particular FIG. 6 therein discloses a drug delivery system comprising a cartridge and a device with a front-loaded cartridge holder adapted to axially receive and hold a cartridge in a loaded position. The cartridge comprises first coupling means arranged at the distal portion, and the cartridge holder comprises second coupling means arranged at the distal portion, wherein the first and second coupling means are configured to engage each other by front-loading when the cartridge is inserted into the cartridge holder by an axial movement that is completed by an angular rotation.

U.S. Pat. No. 9,173,995 describes a front loaded device. Tapered lugs protrudes radially from a syringe barrel that is front loaded into the device—and while the syringe barrel is inserted along a longitudinal axis, the tapered lugs thereof are guided firstly be a first retaining ring and secondly by a second retaining ring which is rotatable and spring loaded about the longitudinal axis. The first retaining ring has protrusions that are tapered to guide the tapered lugs between the protrusions. At the point where the tapered lugs on the syringe barrel have passed the first retaining ring, the second retaining ring, which is rotatable and spring loaded about the longitudinal axis and which also has protrusions, engages with the tapered lugs of the syringe barrel to rotate the syringe barrel to a position where its tapered lugs are moved behind the protrusions of the first retaining ring. By the spring loading, the syringe barrel is kept in a fixed position. The syringe barrel is removed by turning it, thereby overcoming the spring force.

However, these front-loaded drug delivery systems are cumbersome to use since they require that a user uses two hands for the operation of loading the drug delivery system with a cartridge since one hand is needed to hold the device and another is needed to insert and rotate the cartridge. For at least some groups of users this may prevent self-administration use or make own use very cumbersome.

SUMMARY

There is provided an auto injector for administering injection of a medicament from a cartridge containing the medicament, the auto injector comprising:
  a housing; and
  a cartridge receiver with a cartridge receiver compartment configured to receive a cartridge assembly with at least one cartridge retention member when inserted through a cartridge receiver opening along a longitudinal axis; and
  an ejector configured to support the cartridge assembly by being suspended to move along the longitudinal direction and being spring-loaded in the direction opposite of the receiving direction;
wherein the cartridge receiver compartment has a first section, at a first distance from the cartridge receiver opening, with inwardly extending first guide members that extends over first guide member angles and are spaced apart to form a passage at passage angles between the inward first guide members; wherein the inward first guide members form a first bore accepting the cartridge assembly when inserted through the cartridge receiver opening;
wherein one or more of the first guide members has/have a face that faces away from the cartridge receiver opening and forms a concave shape with a slope portion, at slope angles, leading towards a retention portion at or about a bottom portion of the concave shape;
wherein the cartridge receiver compartment has a second section with an annular shape, at a second distance from the cartridge receiver opening, and with second guide members with first faces that are inclined about a radial axis to the longitudinal axis and angularly arranged to extend at least partly over passage angles and protrusion angles;
wherein the second guide member has second faces that are inclined about a radial axis to the longitudinal axis and are arranged alternately with the first faces;
wherein the first faces and the second faces are inclined towards greater distance from the cartridge receiver opening in a direction of rotation being either a clockwise or anti-clockwise direction;
wherein the first faces and the second faces are separated by first riser portions; and wherein the first riser portions are angularly positioned at or within the first guide member angles.

Since the cartridge assembly has at least one cartridge retention member, retention of the cartridge retention member gives retention of the cartridge assembly and thus a cartridge accommodated in the cartridge assembly.

In this way intuitive front loading of an auto injector is enabled. Additional advantages are presented further below.

Retention is achieved in that when the cartridge assembly is inserted, at a first angular position, along the longitudinal axis, the cartridge retention member travels with the cartridge assembly and via the passage it passes between the inwardly extending first guide members and onwards until it lands on the inclined face of one of the second guide members, which by their inclined faces causes a rotation of the cartridge retention member and thus the cartridge assembly from the first angular position to a second angular position as the insertion continues at least until the cartridge retention member has reached the first guide member angles via the inclined face. The cartridge retention member is thus brought 'behind' the first guide members at the second angular position, where the ejector, since it is spring-loaded, presses the cartridge retention member in a direction opposite of inserting the cartridge assembly and against an underside of the first guide members, wherein the underside is a side facing away from the cartridge receiver opening. In this way the cartridge assembly is retained in the cartridge receiver compartment.

The cartridge assembly is typically inserted by a human being inserting the cartridge assembly with a force sufficient to overcome the spring-load acting on the cartridge assembly. At the second angular position the human being may ease the force applied to overcome the spring-load, whereby the spring-load moves the cartridge assembly outwards, but at an angular position where the cartridge retention member and the underside of first guide members restrict the outward movement such that the cartridge assembly is prevented from falling out.

The first section may be arranged closer to the cartridge receiver opening than the second section. The first section and the second section are spaced apart in the longitudinal direction by a clearance exceeding the longitudinal extent of the cartridge retention member such that rotation of the cartridge assembly about the longitudinal axis is possible at least for some longitudinal positions of the cartridge assembly relative to the first and second sections.

In some aspects the spring-load acting on the cartridge assembly is exercised directly or indirectly by a resilient member such as a spiral spring also known as a helical spring.

In some aspects the cartridge assembly, when disregarding the cartridge retention members, is substantially circular. The cartridge receiver compartment may have a substantially round interior.

In some aspects the first bore of the first section is circular or substantially circular. There may be six pairs of a first guide member and a passage annularly arranged about the bore. Pairs of a first guide member and a passage may cover an angle range of e.g. about 60 degrees. In some aspects there are 4, 5, 7 or 8 pairs of a first guide member and a passage. In some aspects the passage covers an angular range of about 15 degrees and the first guide member covers an angular range of about 45 degrees.

The concave shape of the first guide members serve to improve rotational retention of the cartridge assembly when the ejector exercises the spring-load on the cartridge assembly. The cartridge assembly retention member then lands in the concave shape and is retained by the 'slopes' of the concave shape.

The slope portion may be defined by a face inclined towards the insertion opening for a direction of rotation and in the direction of rotation leading towards the deepest point of the concave shape.

The concave shape may be asymmetric about a centre line in the longitudinal direction. The slope portion may comprise a substantially flat portion that is inclined to smoothly rotate the cartridge retention member upon a move along the longitudinal axis, in a direction opposite of insertion, towards the retention angle. The retention portion may in a clockwise or anticlockwise rotation about the longitudinal direction, coherently continue from the slope portion and terminate in a retention face where the cartridge retention member is prevented from further smooth rotation. The retention face may be substantially parallel to the longitudinal axis.

To achieve a desired rotational retention of the cartridge assembly, depth and steepness of the concave shape may be adapted to the shape of the cartridge assembly or vice versa. In some aspects the concave shape is deeper than the radius of a circle circumscribing an end portion of the cartridge retention member.

The at least one of the first faces serves to rotate a cartridge retention member that lands on the first face, upon its travel through the passage, to an angular retention position behind the first guide member i.e. at a first guide member angle; whereas a second face next to the first face serve to further rotate the cartridge retention member, travelling on an outbound journey, from the angular retention position to or towards a passage on the other side of the first guide member that held it in a retention position after its inbound journey. Thus the cartridge retention member is rotated monotonously in the direction of rotation.

In embodiments wherein one or more of the first guide members has/have a face that faces away from the cartridge receiver opening and forms a concave shape with a retention portion at a retention angle about the longitudinal axis and a slope portion at slope angles about the longitudinal axis, at least one of the first faces serves to rotate a cartridge retention member that lands on the first face, upon its travel through the passage, to or towards guide angles of the first guide members. The second faces serve to rotate the cartridge retention member, travelling on an outbound journey, from the retention angle to or towards a passage on the other side of the first guide member that held it in a retention position. The guide portion of the first member serves to make the cartridge retention member pass the riser portion separating the first faces and the second faces.

Due to the inclined faces and the riser portions separating them an annular saw-tooth-like shape is provided. In some aspects the riser portions are substantially parallel to the longitudinal axis. In some aspects the riser portions have substantially the same height.

In some embodiments, the first guide members have a first guide face that faces the cartridge receiver opening and forms a convex pointing shape with an apex directed towards the cartridge receiver opening.

Thereby insertion of the cartridge assembly can start out at any angular position about the longitudinal axis or at least at a wider selection of angles without the cartridge retention members being obstructed by the first guide members and thus prevent the cartridge assembly from further longitudinal movement in the insertion direction.

In case the angular position is such that the cartridge retention members do not align with the passages when the insertion of the cartridge assembly starts out, the cartridge retention members and thus the cartridge assembly smoothly proceed by an angular rotation caused by the pointing shape of the first guide members. This improves the ease of use of the auto-injector also for those with below average motoric skills.

In some aspects the apex has an angle of about 90 degrees, e.g. 70-110 degrees. In some aspects the apex is symmetrically positioned with respect to the angular extent, about the longitudinal axis, of the first guide member; however, it may alternatively be asymmetrically positioned.

In some embodiments, the first section and the second section maintains a fixed angular position with respect to each other. Thereby the passage between the inward first guide members and the guide members remain in a fixed position with respect to the first faces and the second faces. This in turn secures that the one or more cartridge retention members, of the cartridge assembly, are always guided in the same way. This improves the quality of the user's experience of the auto injector.

In some embodiments, one or more of the first guide members has/have a face that faces away from the cartridge receiver opening and forms a concave shape with a guide portion, at slope angles, leading towards a retention portion at or about a retention angle at or about a bottom of the concave shape; wherein one or more first riser portions are angularly arranged at slope angles; and wherein one or more first riser portions are angularly arranged between the retention angle and a centre of passage angles in a direction of rotation being either a clockwise or anticlockwise direction.

The riser portions, in cooperation with the slope portion of the concave shape, enables at least partially that a first movement overcoming the spring-load in an insertion direction leads to retention of the cartridge assembly, whereas a second movement in the same direction, also overcoming the spring-load, leads to a release of the cartridge assembly.

The retention angle may be defined by the bottom of the concave shape. The guide portion may be defined by a face inclined towards the insertion opening for a direction of rotation and in the direction of rotation leading towards the bottom of the concave shape.

The direction of rotation is defined as the either a clockwise or anticlockwise direction in which the first faces are inclined towards greater distance from the cartridge receiver opening.

In some embodiments, one or more of the first faces and the second faces are divided into sections separated by a second riser portion. Such a further riser portion hinders at least to some extend an unintended reverse rotation when the at least one cartridge retention member travels on the first face and second face on an inbound journey.

When the at least one cartridge retention member travels, clockwise or anticlockwise about the longitudinal axis, on the first face on an inbound journey, the first riser portions prevent the cartridge retention member from a further rotation in the respective direction. On the contrary, the second riser portions hinder an unintended reverse rotation to the respective rotational direction. In some aspects the first riser portions are higher than the second riser portions.

In some embodiments, the first guiding member has an eject face that is inclined towards the cartridge receiver opening at angles beyond the retention angle in a direction of rotation being either a clockwise or anticlockwise direction. Thereby it is possible that any passage among the passages formed between the first guide members can be used for insertion leading to retention. Upon a release operation, the eject face guides the cartridge retention member to a neighbouring passage following in a direction of rotation.

In some embodiments, the second guiding members are configured as a first set of steps with treads that are inclined about the radial axis and a second set of steps with treads that are inclined about the radial axis; wherein the treads of the first and second steps are inclined towards greater distance from the cartridge receiver opening for a clockwise or anticlockwise direction of rotation; wherein the treads of the first set of steps are arranged more proximal to the cartridge receiver opening than the treads of the second set of steps; and wherein the first set of steps are alternately arranged with the second set of steps; with riser portions between the steps, forming an annular member comprised by the second section.

When a cartridge retention member lands on a tread it is guided downwards, in the insertion direction, on the inclined tread it landed on towards a neighbouring inclined step out over a riser portion between the steps. The riser portion prevents or at least reduces the risk that a direction of rotation is suddenly reversed during insertion of the cartridge assembly whereby retention may fail and lead to an unsatisfactory user experience.

The treads of the first steps may be angularly arranged as the first faces mentioned above to extend at least partly over passage angles and protrusion angles. In some aspects the treads of the first steps are angularly arranged to extend fully over passage angles. In some aspects the treads of the second steps are angularly arranged within protrusion angles.

In some aspects the steps are arranged such that two, three or four treads extend angularly over the same angles about the longitudinal axis as one passage and a neighbouring one first guide member.

In some embodiments, the first guide members and the second guide members are configured and angularly aligned such that: upon insertion, the cartridge retention member passes the passage in a longitudinal direction, lands on a first section of the first face, by rotation follows the first face out over a second riser portion to a second section, and upon ease of an insertion force: the cartridge retention member travels to the retention portion via the slope portion.

In some embodiments, the first guide members and the second guide members are configured and angularly aligned such that: upon release, e.g. by a user exerting a force, e.g. by pushing, on the cartridge in the direction of insertion, the cartridge retention member leaves the retention position and lands on the first section of the second face, by rotation follows the second face out over a second riser portion to a second section; and upon ease of the force: the cartridge retention member travels to the eject face, wherefrom a the cartridge retention member is guided towards the cartridge receiver opening via a passage.

In some embodiments, the ejector comprises an ejector lock that is operative by one or more of rotation, translational movement and axial movement to move to a position where movement of the ejector is restricted in the direction of insertion. The ejector lock may thereby lock the ejector to prevent it from moving backwards (i.e. in the insertion direction) when the cartridge assembly has been inserted and is in a retention position that prevents it from moving forward (i.e. opposite direction of insertion). Thus despite the front loaded insertion, the cartridge is prevented from moving backwards or forwards when locked as mentioned.

In some embodiments the ejector is configured with: an ejector support face for supporting the cartridge or cartridge assembly, a longitudinal ejector slot extending towards the ejector support face from an ejector rest portion; and an ejector lock supported for turning at least a fraction of a revolution and maintained in a longitudinal position, such as a fixed longitudinal position, relative to the housing; wherein the ejector lock has a ejector lock support portion that is configured to align with and slide along the longitudinal ejector slot at a first angle and to be brought to align with the ejector rest portion at a second angle.

Thereby the ejector rest portion and the ejector lock support member in combination may form a stop that is disengaged at the first angle and engaged at the second angle.

Thus, it is appreciated that, at the second angle, the ejector lock by its turning effectively introduces a stop, by its support member receiving the rest portion. The stop prevents further movement of the rest portion beyond the support member in the receiving direction, if the rest portion is not otherwise prevented from landing on the support member. Thus, the stop contributes to prevent the cartridge from movement beyond a stop position, relative to the housing, in the receiving direction.

At least when the needle of the cartridge assembly penetrates a being's skin a force is transferred from the needle to the cartridge and works to push the cartridge backwards in the receiving direction against the stop when it is engaged. The stop at least contributes to maintaining the position of the cartridge since otherwise precise dose administering may be obstructed.

When the ejector, by means of the stop, sits at the stop position, its ejector support face supports that an end portion of the cartridge or cartridge assembly rests thereon to prevent unintended movement in the receiving direction.

The auto injector enables convenient front-loading of a cartridge accommodated in a cartridge assembly. Since the needle on the cartridge assembly may be protected by a needle cover reliably attached to the cartridge assembly, there is no increased risk of being injured by the needle while loading the auto injector with a cartridge accommodated in a cartridge assembly.

The auto injector enables convenient front-loading by: overcoming the spring-loaded bias when the cartridge meets the support face of the ejector, guiding the cartridge retention members from the passage to a position where the cartridge is prevented from moving out of the cartridge receiver, and turning the ejector lock to prevent movement beyond the stop in the receiving direction such that the cartridge maintains its position in the housing when a pressure on the needle in the receiving direction is at least partially transferred to the cartridge. It is important that the cartridge maintains its position since otherwise precise dose administering is obstructed.

It is appreciated that various distances should be dimensioned such that the support face of the ejector lock abuts the rest portion of the ejector when the cartridge sits in the retention position. Thereby the cartridge is locked or is in a locked position being prevented both from a forward movement and a backward movement, wherein the backward movement is the same as the receiving direction. The cartridge is locked when the stop is engaged i.e. when the ejector lock is at the second angle, whereas the cartridge is unlocked when the stop is disengaged i.e. when the ejector lock is at the first angle.

In some aspects the ejector lock support member extends axially from a wall of the ejector lock, e.g. in the form of a pin, to support the ejector at a transversely extending ejector rest portion. In some aspects the ejector lock support member extends transversely along a rim or edge of the ejector lock to support the ejector at transversely extending ejector rest portion or at an axially extending rest portion.

In some aspects one or more of the ejector lock support portion, the ejector rest portion and the ejector slot are recessed into the ejector lock or the ejector.

It is appreciated that the ejector lock is supported e.g. in a bearing that allows the lock to turn or be turned, at least a fraction of a revolution, while preventing a longitudinal movement.

In some embodiments, the ejector comprises an ejector rod configured with one or more ejector cut-outs to form one or more ejector cogs between the ejector cut-outs; and wherein the ejector lock is configured with one or more ejector lock cogs between one or more ejector lock cut-outs, respectively.

Thereby the one or more ejector cogs may abut with the one or more ejector lock cogs to form the stop when engaged. The stop is engaged by aligning the cogs of the ejector and the ejector lock. Turning of the ejector lock at least a portion of a revolution about the longitudinal axis may disengage the stop whereby the ejector cogs can be accumulated in the ejector lock cut-outs. In this way the cogs and the cut-outs form complementary cogs and cut-outs.

The one or more cogs of the ejector rod and the one or more complementary cut-outs of the ejector lock are arranged at angular ranges about the longitudinal axis such that a cog can be accommodated in its entirety or partially by a complementary cut-out. A cog may extend over e.g. 45 degrees and a complementary cut-out may extend over 45 degrees plus an angular range to allow a clearance when the ejector rod and thus the cog moves in the longitudinal direction in or out of the cut-out of the ejector lock.

The angles at which cut-outs, cogs and complementary cogs and cut-outs are located implicitly define the first angular position where the ejector lock and ejector rod mutually are angularly positioned to allow movement of the cartridge assembly in the receiving direction, and the second angular position where the ejector lock and ejector rod mutually are angularly positioned to restrict movement of the cartridge assembly in the receiving direction at least restricted from moving beyond a predefined longitudinal position.

In the second angular position, at least one cog of the ejector rod abuts end-to-end at least one cog of the ejector lock; whereas in the first angular position, the at least one cog of the ejector rod is accommodated in a complementary cut-out.

The ejector cogs have end portions denoted an ejector rest portion and the ejector lock cogs have end portions denoted an ejector lock support portion.

The ejector lock support portion supports the ejector rest portion when the stop is engaged.

Thus the cogs have respective end portions which abut one another when the stop is engaged. Cut-outs of the ejector rod and cut-outs of the ejector lock have respective bottom portions. The bottom portions may extend between side portions separating cogs and cut-outs.

At a longitudinal position of the ejector rod where the cogs abut one another, the ejector defines by its length relative to the ejector lock at which position the cartridge or cartridge assembly is restricted from further movement by means of the stop in the receiving direction. The ejector may be suspended by a resilient member to move in the opposite direction of the receiving direction, in which case the cogs of the ejector rod travels away from the cogs of the ejector lock.

In some aspects the ejector rod has four cogs and four cut-outs and the ejector lock has four complementary cogs and four complementary cut-outs.

This gives a good trade-off between the amount of rotation needed to turn the ejector rod and the ejector lock relative to each other from a securely locked position to an open position and mechanical robustness of the cogs.

In some aspects the cogs and cut-outs have an even angular size, e.g. 45 degrees or 60 degrees—in both cases minus an angular range to allow a clearance between a cog and a cut-out.

In some embodiments, one or more of the cut-outs and the cogs have a substantially rectangular shape.

Thus, the one or more cut-outs, such as ejector cut-outs and/or ejector lock cut-outs have edges orthogonal to the longitudinal axis and edges along the longitudinal axis. Due to the edges along the longitudinal axis a good engagement for retaining a relative angular position between the ejector rod and the lock is obtainable at least when the stop is engaged.

In some aspects thereof the ejector cut-outs accommodate ejector lock cogs and ejector lock cut-outs accommodate ejector cogs in a complementary manner such that spaces are substantially filled out between cogs to resemble a cylindrical object. However, an angular clearance is typically needed between cogs to allow sufficiently low friction of a longitudinal movement and to allow for variations occurring during manufacture of the ejector and ejector lock.

In some embodiments the auto injector comprises a plunger rod operative by movement along the longitudinal axis to exercise a pressing force on a cartridge accommodated in the cartridge assembly. The plunger rod may be configured to move a first stopper of the cartridge to expel at least a part of the medicament from the cartridge.

In some embodiments the plunger rod is accommodated in the ejector to be longitudinally displaceable. Thereby the ejector may support the cartridge along a rim thereof, whereas the plunger rod may actuate movement of the first stopper of the cartridge to expel at least a part of the medicament from the cartridge.

In some embodiments the ejector lock comprises an ejector lock guide pin configured to engage with a plunger rod track provided in the plunger rod, such that longitudinal movement of the plunger rod, at least over a predefined range, inflicts a turning of the ejector lock about the longitudinal axis.

In some embodiments the plunger rod track comprises at least one track portion that guides the ejector lock guide pin from a first angle to a second to turn an ejector lock from the first angular position to the second angular position.

In some embodiments the auto injector comprises an operational module configured to: engage the plunger rod to move along the longitudinal axis to exercise a pressing force on a cartridge accommodated in the cartridge assembly; and engage an ejector lock by one or more of rotation, translational movement and axial movement to move to a position where movement of the ejector is restricted in the direction of insertion.

Thereby a human being may insert and remove a cartridge assembly manually by two respective but very similar movements one after the other, before and after injection of a medicament contained in the cartridge carried in the cartridge assembly. Once inserted, automatic or manual activation of the operational module may trigger automatic engagement of the ejector lock and the plunger rod to assist the human being in injecting his/hers medicament. An operational module may comprise one or more electric motors that engage the plunger rod and the ejector lock.

BRIEF DESCRIPTION OF THE FIGURES

A more detailed description follows below with reference to the drawing, in which.

DETAILED DESCRIPTION

Figure 1:
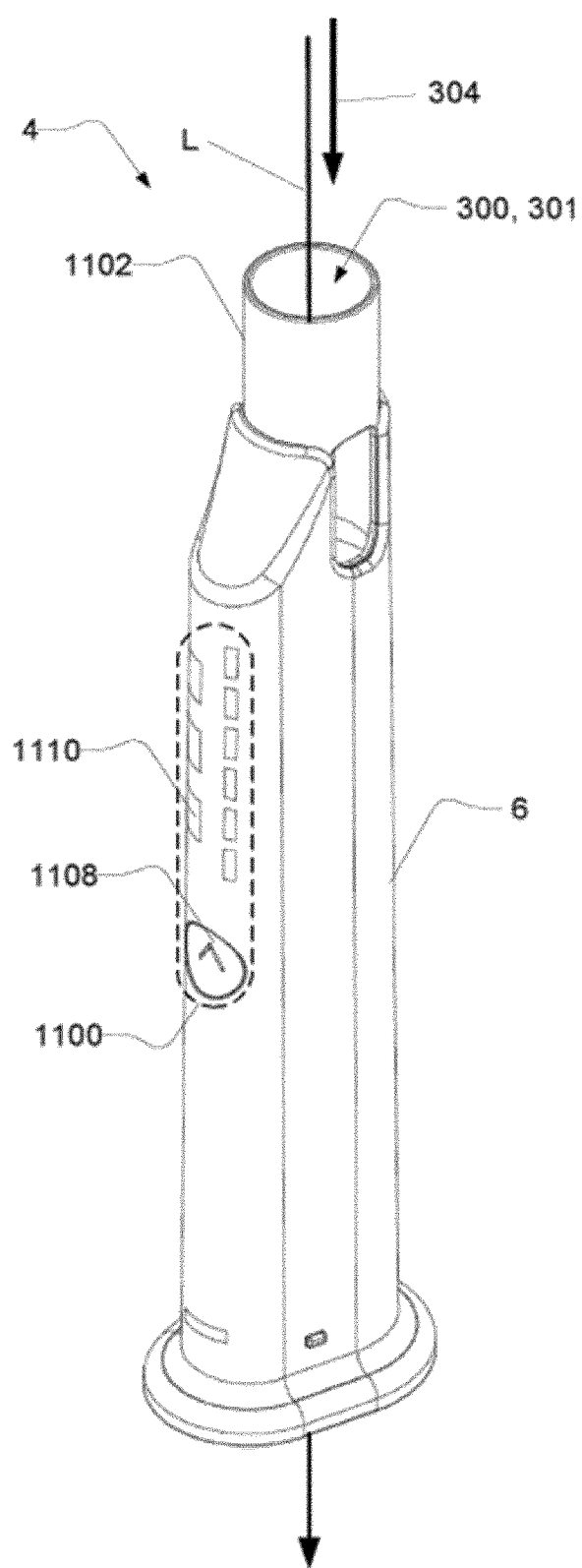
FIG. 1 shows an auto injector.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The term 'user' refers to a human being using the auto injector for self-administering a medicament. In this respect the user may also be designated a 'patient'. Thus, one use case of the auto injector is self-administration of a medicament. The auto injector is described with this use case in mind. However, in another use case an assistant, e.g. a nurse or home carer, may operate the auto injector to administer the medicament into the patient. The latter use case is also enabled by the present disclosure of the auto injector. The user may use the auto injector in connection with his or hers daily activities.

FIG. 1 shows an auto injector. The auto injector 4 may be configured for administering a medicament. The auto injector 4 may be an electronic auto injector.

The auto injector 4 comprises a housing 6. The auto injector 4 comprises a cartridge receiver 300. The cartridge receiver is configured to receive a cartridge and/or a cartridge assembly comprising a cartridge. The cartridge may contain the medicament.

The cartridge receiver 300 has a cartridge receiver opening 301. The cartridge receiver 300 is configured to receive the cartridge and/or the cartridge assembly through the cartridge receiver opening 301 in a cartridge receiving direction 304 along a longitudinal axis, L.

The auto injector 4 may comprise a user interface 1100, as illustrated. The auto injector 4 comprises a trigger member, such as the contact member 1102. The contact member 1102 may be configured to be pressed against an injection site on a patient's skin. The contact member 1102 may be movable in the cartridge receiving direction 304, relative to the housing, if pressed against the injection site. The contact member 1102 may be part of the user interface 1100.

The user interface 1100 comprises a first input member 1108, e.g. a button. The first input member 1108 may provide for a user input from a user. For example, the first input member 1108 may be used for receiving a push from a user to proceed to a next step.

The user interface 1100 comprises a first output member 1110 as illustrated, e.g. a plurality of LEDs. The first output member 1110 may provide for a user output to a user. The user interface 1100 may comprise a second output member (not shown), e.g. a speaker. The second output member may be configured to provide audible output to the user. For example, the first output member 1110 and/or the second output member may be used to indicate a step in the procedure to the user and/or to indicate an error message.

The auto injector 4 may comprise a cover (not shown) to protect the auto injector from dirt and filth when not in use.

Figure 2:
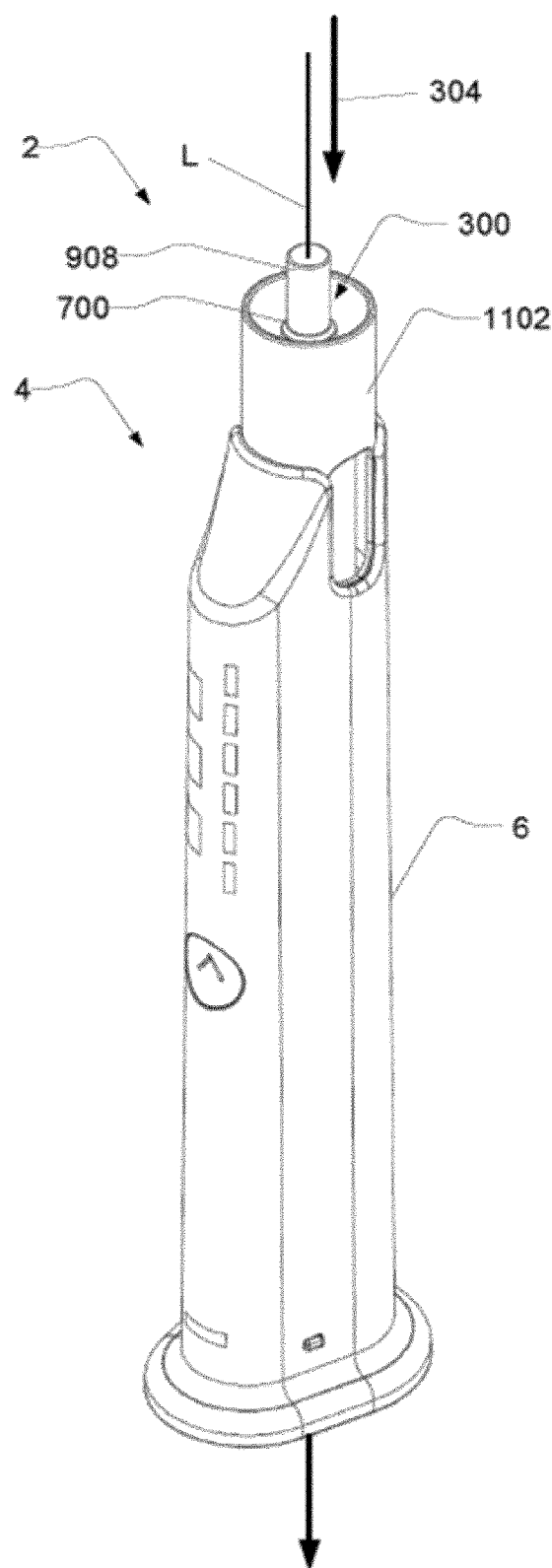
FIG. 2 shows the auto injector with a cartridge.

FIG. 2 shows the auto injector with a cartridge. The system 2 comprises an auto injector 4, as described in relation to FIG. 1, and an exemplary cartridge 700 received in the cartridge receiver 300 by front loading. The cartridge 700 is shown with a needle cover 908. The needle cover 908 extends out of the contact member 1102 to allow removal of the needle cover 908 from the cartridge 700.

By front loading is understood that at least the cartridge 700 is received with its needle end pointing out of the cartridge receiver opening 301. When the cartridge is being inserted and especially when it is fully inserted or almost fully inserted, the cartridge or cartridge assembly may be substantially covered by the housing or the contact member 1102. Especially in this situation the needle cover 908 serves as a protective means that makes it possible for a user at least to press on the needle cover 908 or a tip thereof to fully insert the cartridge without being injured by the needle. When the cartridge is fully inserted and sits in a retention position it is possible to detach the needle cover such that the auto injector is ready for use to inject the medicament or a portion thereof contained in the cartridge. After use, i.e. when a dose of medicament has been injected, the needle cover is attached such that the needle cover again serves as a protective means that makes it possible for a user at least to press on the needle cover 908 or a tip thereof to remove the cartridge without being injured by the needle.

Figure 3:
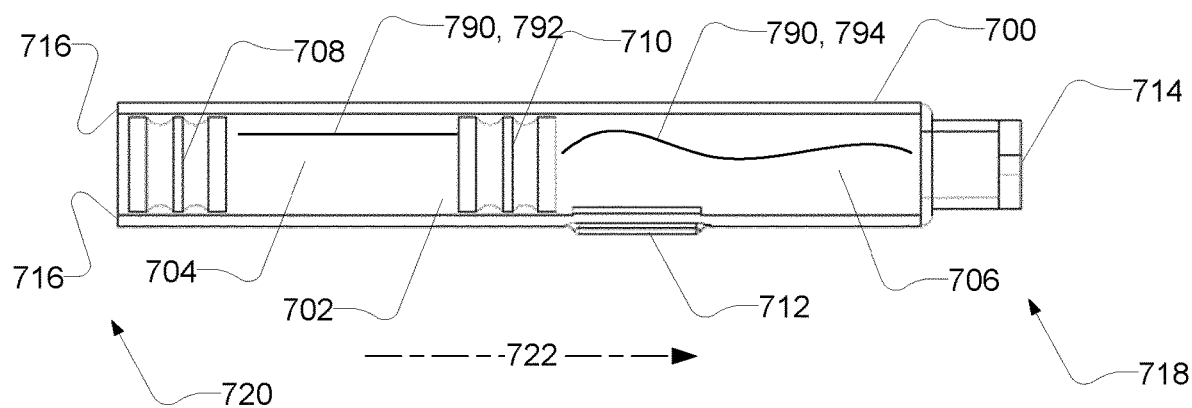
FIG. 3 shows a cartridge.

FIG. 3 shows a cartridge, such as a cartridge 700 being configured to be received in the cartridge receiver of an auto injector, such as the auto injector described in relation to the preceding figures.

The cartridge 700 comprises a cartridge compartment 702. The cartridge compartment 702 may be configured for containing a medicament. The cartridge 700 has a first end 718 and a second end 720. The cartridge 700 comprises a cartridge outlet 714 at the first cartridge end 718. The cartridge may be configured to expel medicament through the cartridge outlet 714. The cartridge outlet 714 may be sealed by a needle penetrable sealing. The sealing may be made from rubber and optionally comprise a piercing which enables the needle to penetrate the sealing, while sealing the medicament when the needle is not penetrating the sealing.

The cartridge comprises a first stopper 708 movable inside the cartridge compartment, e.g. in a first stopper direction 722, e.g. towards the first cartridge end. For example, the medicament may be expelled through the cartridge outlet 714 upon movement of the first stopper 708 in the first stopper direction. The cartridge comprises a cartridge back face 716 at the second cartridge end. The cartridge back face 716 comprises a cartridge back end opening for providing access to the first stopper 708 for a plunger rod.

As illustrated, the cartridge 700 may be a dual chamber cartridge. The cartridge comprises a second stopper 710 movable inside the cartridge compartment 702, e.g. in the first stopper direction 722, e.g. towards the first cartridge end. The cartridge compartment 702 comprises a first cartridge sub-compartment 704 and a second cartridge sub-compartment 706. The first cartridge sub-compartment 704 is between the first stopper 708 and the second stopper 710. The second cartridge sub-compartment 706 is between the second stopper 710 and the cartridge outlet 714. The cartridge comprises a bypass section 712 for providing fluid communication between the first cartridge sub-compartment and the second cartridge sub-compartment. The bypass section 712 provides fluid communication between the first cartridge sub-compartment and the second cartridge sub-compartment when the second stopper 710 is positioned in the bypass section 712.

The first cartridge sub-compartment 704 contains a first medicament component 792 of the medicament 790. The first medicament component 792 may be a liquid as illustrated. The second cartridge sub-compartment 706 contains a second medicament component 794 of the medicament 790. The second medicament component 794 may be a powder composition. By positioning of the second stopper 710 within the bypass section 712, the first medicament component 792 may be transmitted into the second cartridge sub-compartment 706 via the bypass section 712, thereby mixing the first medicament component 792 and the second medicament component 794 to achieve the combined medicament 790.

The cartridge 700 may generally have a cylindrical form. However, the by-pass section 712 may form a protrusion from the generally cylindrical form.

Figure 4:
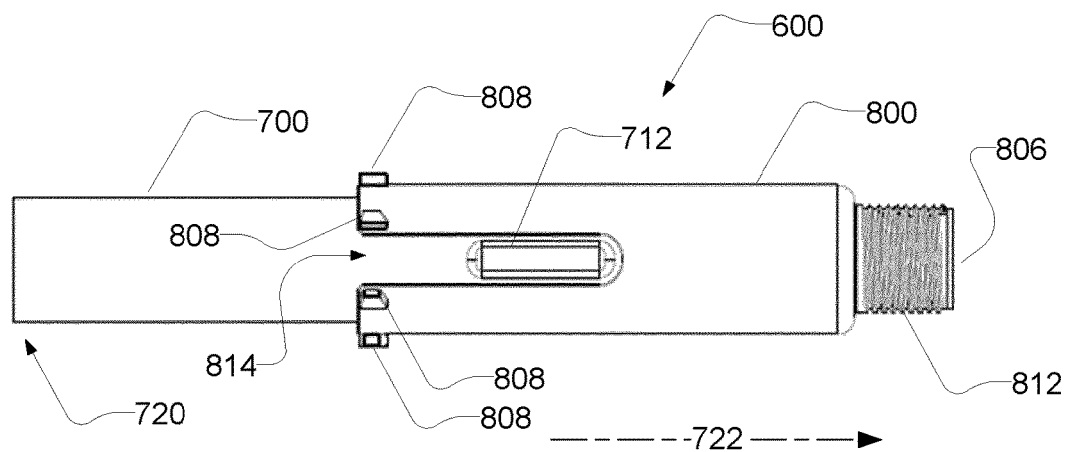
FIG. 4 shows a cartridge holder with a cartridge.

FIG. 4 shows a cartridge holder with a cartridge. The cartridge holder 800 accommodates at least a portion of the cartridge 700 by frictional coupling. Like the cartridge 700, the cartridge holder 800 may have a generally cylindrical form. An inner diameter of the cartridge holder 800 matches with an outer diameter of the cartridge. The cartridge holder may be made from a plastics material, whereas the cartridge typically is made from glass or a glass-like material; the cartridge may also be made from a plastics material.

As shown, the cartridge holder 800 accommodates the first cartridge end 718 of the cartridge. The cartridge holder 800 has a cartridge holder slot 814 which accommodates the by-pass section 712 which is shown in FIG. 3 as a protruding member. The cartridge holder introduces coupling options to the cartridge in the form of a needle assembly coupling portion 812, which as shown may take the form of a threading, and cartridge retention members 808. The cartridge retention members 808 may take the form of protrusions that extends from the generally cylindrical form of the cartridge holder 800. The cartridge retention members 808 may be located at or close to the rim of the cartridge holder at the opposite end of the cartridge assembly outlet opening 806. In some embodiments the cartridge retention members 808 are arranged at a greater distance from the rim than shown.

The needle assembly coupling portion 812 makes it possible to couple the cartridge 700, via the cartridge holder 800, to a needle assembly as will be described in greater detail below.

Figure 5:
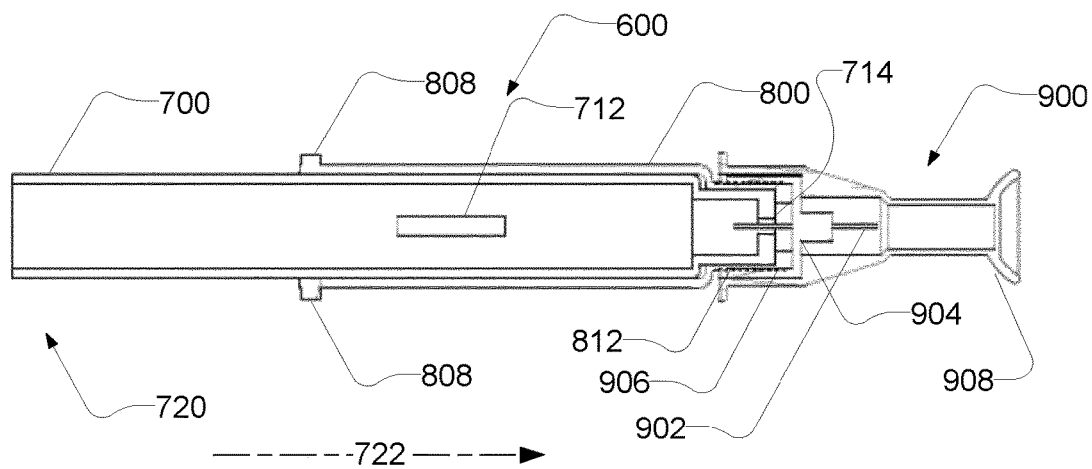
FIG. 5 shows a cross section of a cartridge assembly with a needle assembly.

FIG. 5 shows a cross section of a cartridge assembly with a needle assembly. Note that the cartridge 700 is shown without stoppers, but with the by-pass section 712.

The needle assembly 900 is coupled to the cartridge holder by a respective needle assembly coupling portion 812 and cartridge holder coupling portion 906 of the needle assembly and the cartridge holder. The coupling portions 812 and 906 may be in the form of threading.

The needle assembly 900 comprises a needle hub 904 that holds a needle 902. The needle hub 904 may have a bore at its one end into which the needle extends and on sidewalls of which the needle assembly coupling portion 812 is arranged. The needle assembly 900 also comprises a needle cover 908 that may be coupled by frictional coupling to the needle hub.

Figure 6:
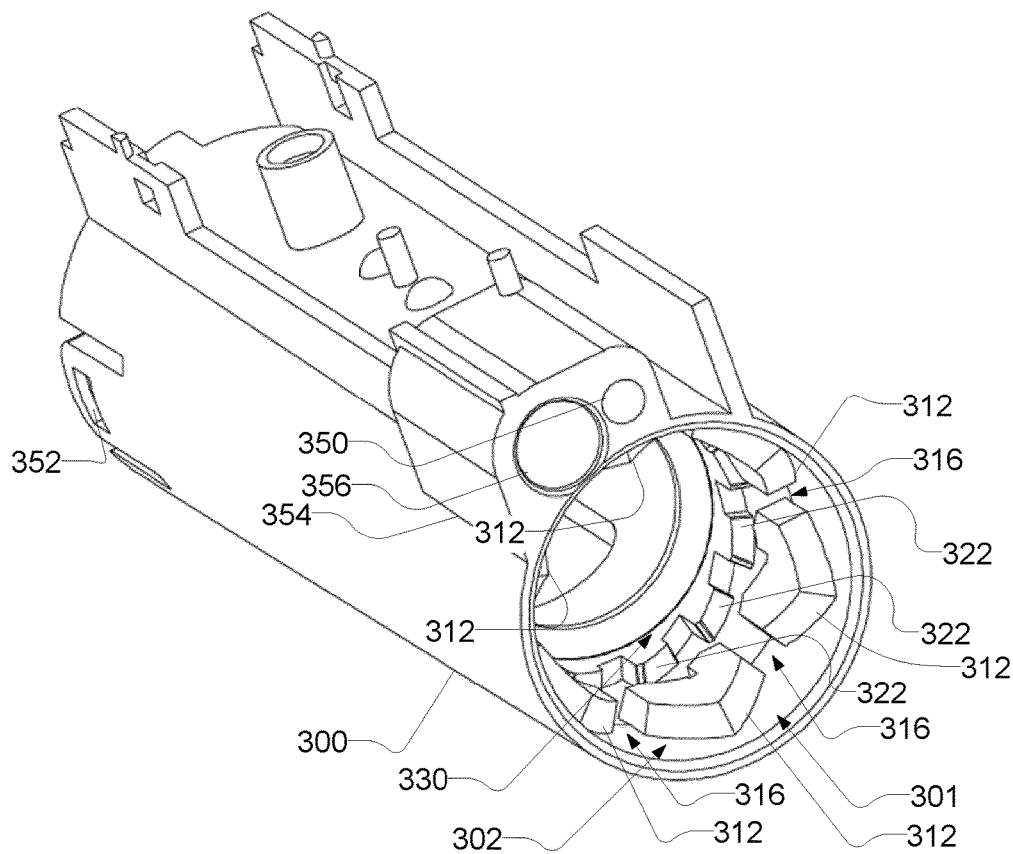
FIG. 6 shows a cartridge receiver.

FIG. 6 shows a cartridge receiver. The cartridge receiver 300 has a cartridge receiver compartment 302 configured to receive a cartridge assembly 600 through a cartridge receiver opening 301. The cartridge receiver compartment 302 has a first section, at a first distance from the cartridge receiver opening 301, with inwardly extending first guide members 312 that are spaced apart to form passages 316 between the inwardly extending first guide members 312. The inwardly extending first guide members 312 form a first bore accepting the cartridge assembly 600 when inserted through the cartridge receiver opening 301. The diameter of the bore is slightly larger than an outer diameter of the cartridge assembly 600 excluding the cartridge retention members 808, but is smaller than the diameter of a circle circumscribing the cross section of the cartridge assembly 600 and the cartridge retention members 808. The cartridge retention members 808 can thereby not pass a first guide member 312 unless the cartridge is turned about the longitudinal axis, L, such that the cartridge retention members pass through the passages 316.

The cartridge receiver compartment 302 has an additional second section, with an annular shape, at a second distance, more remote than the first distance, from the cartridge receiver opening 301. The second section has second guide members 322. The second guide members 322 are arranged with inclined faces and at angular positions about the longitudinal axis such that a cartridge retention member 808 having passed the passage 316 next to a first guide member 312 in the receiving direction is guided behind the first guide member 312 by an angular turning about the longitudinal axis, L.

The second guide members 322 form a second bore also accepting the cartridge assembly 600. The diameter of the second bore is substantially the same as the first bore, i.e. slightly larger than an outer diameter of the cartridge assembly 600 excluding the cartridge retention members 808, but smaller than the diameter of a circle circumscribing the cross section of the cartridge assembly 600 and the cartridge retention members 808. The cartridge retention members 808 can thereby not pass a second guide member 322. So when a cartridge retention member 808 lands on the second guide members 322, a turning of the cartridge assembly is inflicted.

The cartridge receiver 300 comprises flanges and coupling means such as opening 352 for coupling to other components of the auto injector (not shown). The cartridge receiver 300 also comprises a base 354 comprising a bore 356 for a spring (not shown) providing a spring-bias to the contact member 1102, which may be guided by a guide rod (not shown) accommodated in a bore 350.

Figure 7:
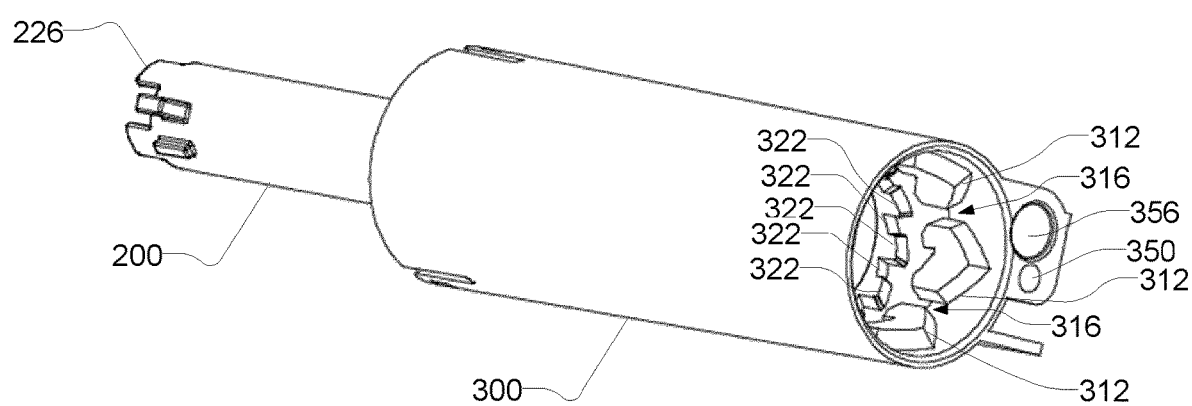
FIG. 7 shows the cartridge receiver with an ejector.

FIG. 7 shows the cartridge receiver with an ejector. In this view the cartridge receiver 300 is shown in a different perspective than in FIG. 6. It is shown that an ejector 200 extends out of the cartridge receiver 300 from the other end of the cartridge receiver than the cartridge receiver opening end.

Figure 8A:
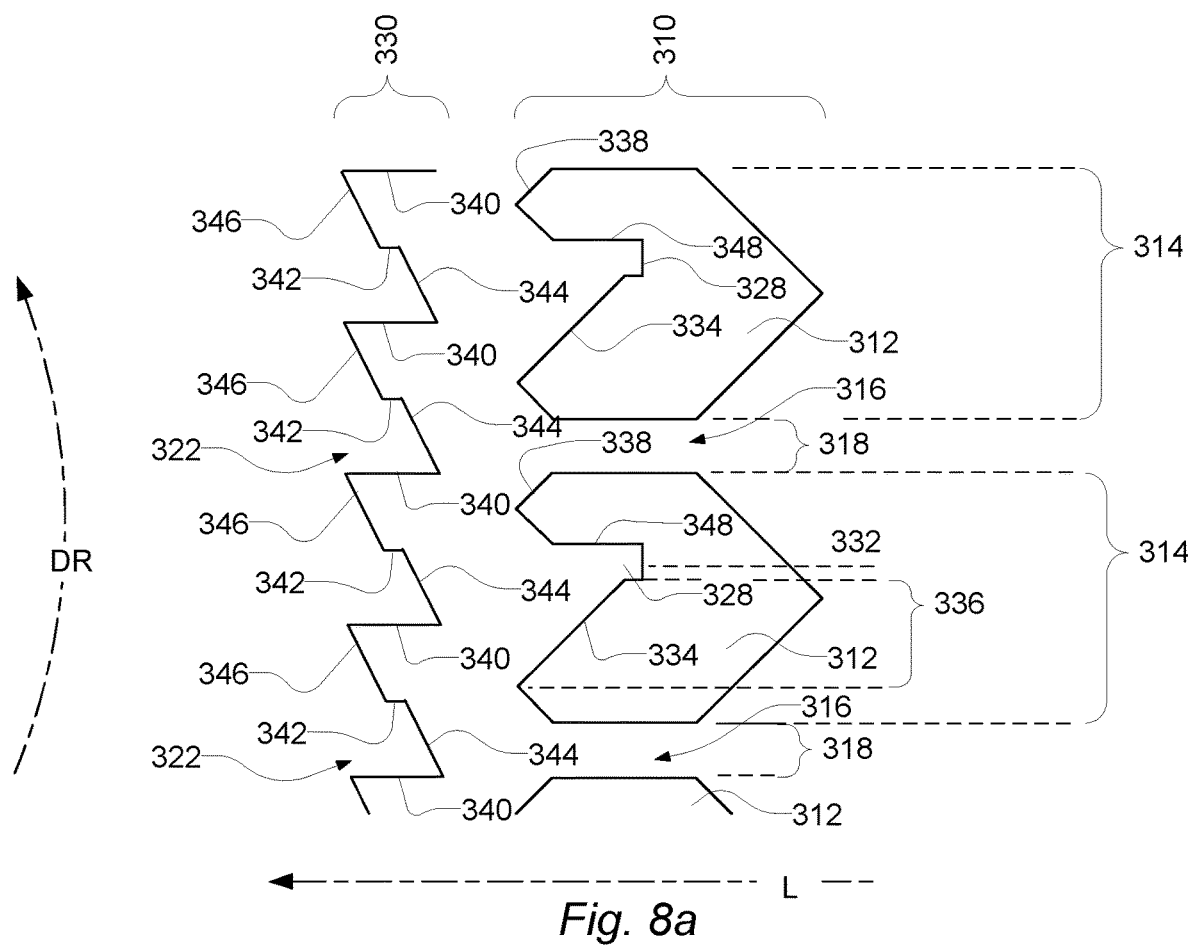
FIG. 8a shows a detailed view of the first section and second section of the cartridge receiver compartment.

FIG. 8a shows a detailed view of the first section and the second section of the cartridge receiver compartment. In this view, portions of the first section 310 and the second section 330 are cut up along the longitudinal axis and fold out from their generally annular shape. The functional aspects of the first section and the second section are described in connection with FIG. 8b below. The dashed line at the bottom of FIG. 8a indicates the orientation of the longitudinal axis, L, and points in the receiving direction, which in this depiction is to the left. The cartridge receiver opening (not shown in this depiction) is located towards the right hand side. Thus, the first section 310 is arranged closer to the cartridge receiver opening than the second section 330. The curved dashed line to the left, DR, indicates a direction of rotation about the longitudinal axis when the first section 310 and the second section 330 are arranged as annular members.

The first section 310 comprises first guide members 312 and the second section 330 comprises second guide members 322.

The first guide members 312 extends over first guide member angles 314 and are spaced apart to form passages 316 at passage angles 318 between the first guide members 312.

Figure 10:
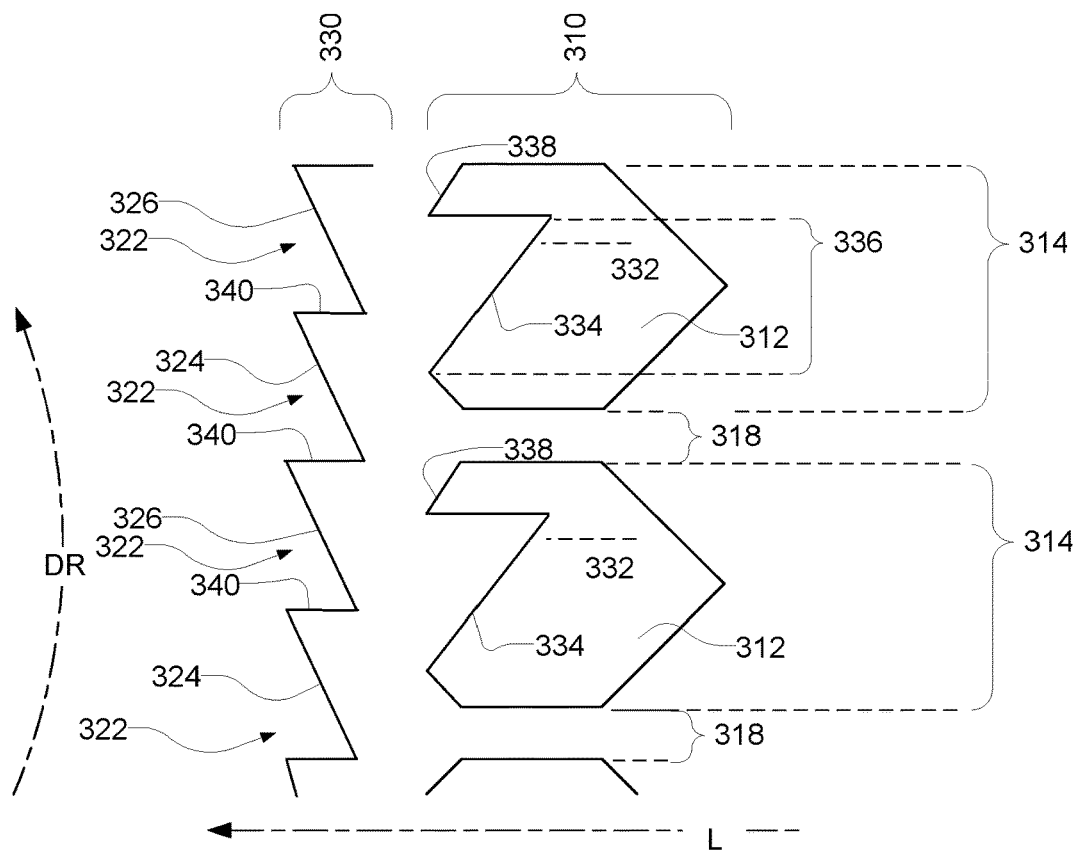
FIG. 10 shows a detailed view of alternative first section and second section of the cartridge receiver compartment.

The second guide members 322 have first faces 324 and second faces 326 (cf. FIG. 10). The first faces and the second faces are arranged alternately and separated by first riser portions 340. The first faces are, in the exemplary embodiment of FIG. 8a, divided into sections 344 and 346 separated by a second riser portion 342. Similarly, the second faces are, in the exemplary embodiment of FIG. 8a, divided into sections 344 and 346 separated by second riser portions 342. The first faces are inclined about a radial axis to the longitudinal axis and angularly arranged to extend at least partly over passage angles 318 and first guide member angles 314.

The first guide members 312 have a first guide face that faces the cartridge receiver opening, i.e. to the right hand side in this depiction, and forms a convex pointing shape with an apex directed towards the cartridge receiver opening.

The first guide members 312 also have a face that faces away from the cartridge receiver opening, i.e. to the left hand side in this depiction, and forms a concave shape with a slope portion 334, at slope angles 336, leading towards a retention portion 328 at or about a bottom portion of the concave shape at a retention angle 332. The slope portion 334 is inclined relative to the longitudinal axis and relative to the orthogonal thereto such that a turning of the cartridge is inflicted when a cartridge retention member 808 is pushed towards the slope portion 334 by a spring-loaded ejector 200. The turning brings the cartridge retention member 808 to the retention portion 328. To limit further turning of the cartridge assembly, a retention face 348 is provided substantially along the longitudinal axis.

Further, the first guide members 312 also have an eject face 338 with a slope that is inclined relative to the longitudinal axis and relative to the orthogonal thereto such that a turning of the cartridge is inflicted when a cartridge retention member 808 is pushed towards the slope portion 338 by a spring-loaded ejector 200.

Figure 8B:
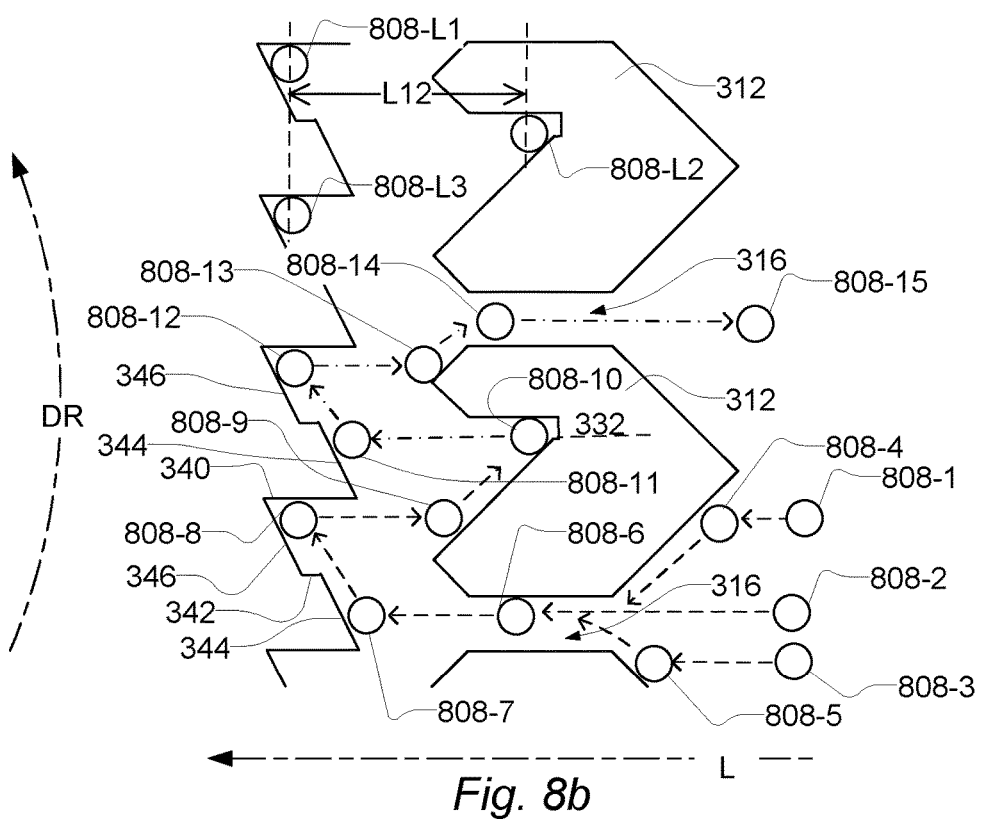
FIG. 8b shows an inbound journey and an outbound journey of a cartridge retention member.

FIG. 8b shows an inbound journey and an outbound journey of a cartridge retention member. The cartridge retention member 808 is depicted as an object with a circular cross section, e.g. in the form of a guide pin, but it may have other forms. The cartridge retention member 808 is shown at different positions indexed by a numeral following the reference numeral; for instance 808-1 indicates the position of the cartridge retention member 808 at position 1.

Dashed lines indicate a so-called inbound journey of the cartridge retention member 808 and dashed-dotted lines indicate a so-called outbound journey. To avoid cluttering the figure, not all reference numerals are inserted, however the reference numerals used in FIG. 8a apply to FIG. 8b for like-shaped elements.

When a cartridge assembly 600 with a cartridge retention member 808 is inserted, starting out in the receiving direction, the cartridge retention member 808 follows an inbound journey. As examples the inbound journey may start at position 1 or position 2 or position 3 at different angles. At position 2 the cartridge retention member 808 may pass straight into the passage 316 to position 6, whereas at position 1 the first guide member 312 inflicts a turning of the cartridge retention member, starting at position 4, where the cartridge retention member lands on the first guide member and continuing by the inflicted turning and longitudinal movement such that it is guided into the passage 316. Also at position 3 on the other side of the passage 316, a first guide member 312 inflicts a turning of the cartridge retention member, starting at position 5, where the cartridge retention member lands on the first guide member and continuing by the inflicted turning and longitudinal movement such that it is guided into the passage 316. Thus, substantially irrespective of the angle at which the cartridge retention member is received, it is guided into the passage 316.

Continuing its journey from a position, such as position 6, in the passage, in the receiving direction, the cartridge retention member lands on a second guide member 322 of the second section 330 and in particular on a first section 344 thereof. Due to the inclined face of the first section 344, a turning of the cartridge retention member 808 is inflicted, such that the cartridge retention member 808 turns from position 7 to position 8, where it meets one of the first riser portions 340 which prevents further rotation. At this position, a user inserting the cartridge assembly will feel that the cartridge assembly stops moving, and will therefore intuitively release the force used for insertion. At this position 8, a release of the force will make the spring-loaded ejector push the cartridge assembly and the cartridge retention member 808 outwards, opposite the receiving direction, to position 9. At position 9 the cartridge retention member 808 lands on the slope portion 334 of a first guide member 312 leading towards the retention portion 328 at or about a bottom portion of the concave shape at a retention angle 332. Due to the spring-loaded ejector working to push the cartridge retention member 808 outwards, the cartridge retention member 808 and hence the cartridge stays in a retention position, position 10.

It should be noted that as the cartridge retention member travels out over the second riser portion 342, it passes a point of no return and the inbound journey is generally not reversible. So, should the user ease the force used for insertion before position 8, but after the point of no return, the cartridge still ends up in the retention position.

While in the retention position the cartridge and the cartridge assembly may be prevented from moving in the receiving direction by a lock that introduces a stop. Thereby the cartridge stays in its retention position even if a force overcoming the spring-load on the cartridge or cartridge assembly is overcome e.g. while the needle penetrates the skin. When the lock is released again to remove the stop, an outbound journey can start.

An outbound journey starts out from position 10 and is initiated when the spring-loaded force is overcome in the receiving direction, e.g. by a user pressing on a needle cover of the cartridge assembly. The cartridge retention member then lands on the second face 326 (cf. FIG. 10) and in particular a first section 344 thereof at position 808-11. Therefrom, it is brought to position 12. At this position, a user ejecting the cartridge assembly will feel that the cartridge assembly stops moving, since the cartridge retention member 808 meets a first riser portion 340, and will therefore intuitively release the force used for ejecting the cartridge assembly. In releasing the force, the spring-loaded ejector will push the cartridge assembly and the cartridge retention member 808 outwards, opposite the receiving direction, to position 13, where the cartridge retention member 808 meets an eject face 338 that guides the cartridge retention member 808 towards a position 14 in the passage 316 and onwards to a position 15 where the cartridge assembly is fully ejected and can be handled as needed e.g. to remove the cartridge from the cartridge assembly and dispose the cartridge.

It is noted that the direction of rotation, DR, is defined by the direction of the slopes of the first face and second face since they define in which direction turning is inflicted.

With respect to the length of an ejector rod 202 and the length of ejector cogs 226 thereof, to be explained in greater detail further below, it is noted that the cartridge retention member 808 should be allowed to travel between a first and a second extreme positions, L1 and L2, spaced apart at a longitudinal distance L12. At the position L2, the cartridge retention member 808 is at its retention position, i.e. an advanced position towards the cartridge receiver opening. At the position L1, the cartridge retention member 808 is at a 'deepest' position, in the receiving direction, given by the second face 326 or section 346 thereof. Thus, the ejector should be able to travel the distance L12. In some embodiments the position L3 may be located at a 'deeper' position than L1, in which case the ejector should allow the cartridge assembly retention member 808 to travel between L3 and L2.

Figure 9A:
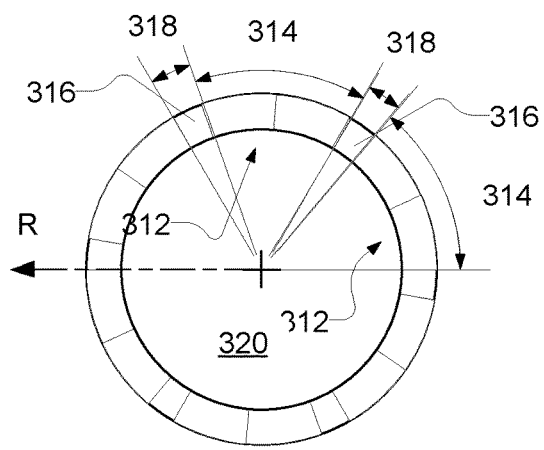
FIG. 9a and FIG. 9b are cross-sectional views of the first section and second section of the cartridge receiver compartment.

FIG. 9a is a cross-sectional view of the first section of the cartridge receiver compartment. This cross-sectional view is orthogonal to the longitudinal axis and shows first guide member angles 314 and passage angles 318 that extend over the first guide members 312 and the passage 316, respectively. The outwardly pointing apex of the first guide members is shown at a centre angle of the first guide member angles 314. The first bore is indicated by reference numeral 320.

The arrow designated by capital 'R' indicates a radial axis orthogonal to the longitudinal axis.

Figure 9B:
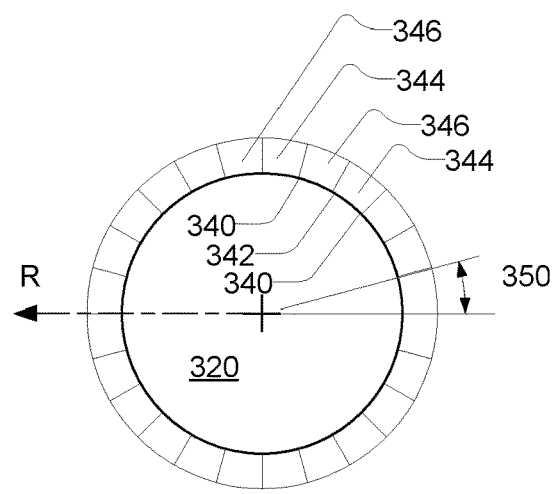

FIG. 9b is a cross-sectional view of the second section of the cartridge receiver compartment. This cross-sectional view is orthogonal to the longitudinal axis and shows the first sections 344 and the second sections 346 separated by first riser portions 340 and second riser portions 342.

Each of one of the first sections 344 and each of one of the second sections 346 may extend over section angles. Section angles may by e.g. about 15 degrees.

FIG. 10 shows a detailed view of alternative first section and second section of the cartridge receiver compartment. The first guide members 312 of the first section 310 have a concave shape with a slope 334 that extends across the retention angle 332.

The second guide members 322 of the second section 330 comprises a first face 324 that extends at least partly over passage angles 318 and first guide member angles 314. A second face 326 extends between first faces, alternately. The first riser portions 340 separate the first faces 324 and the second faces 326.

Figures 11, 12, 13:
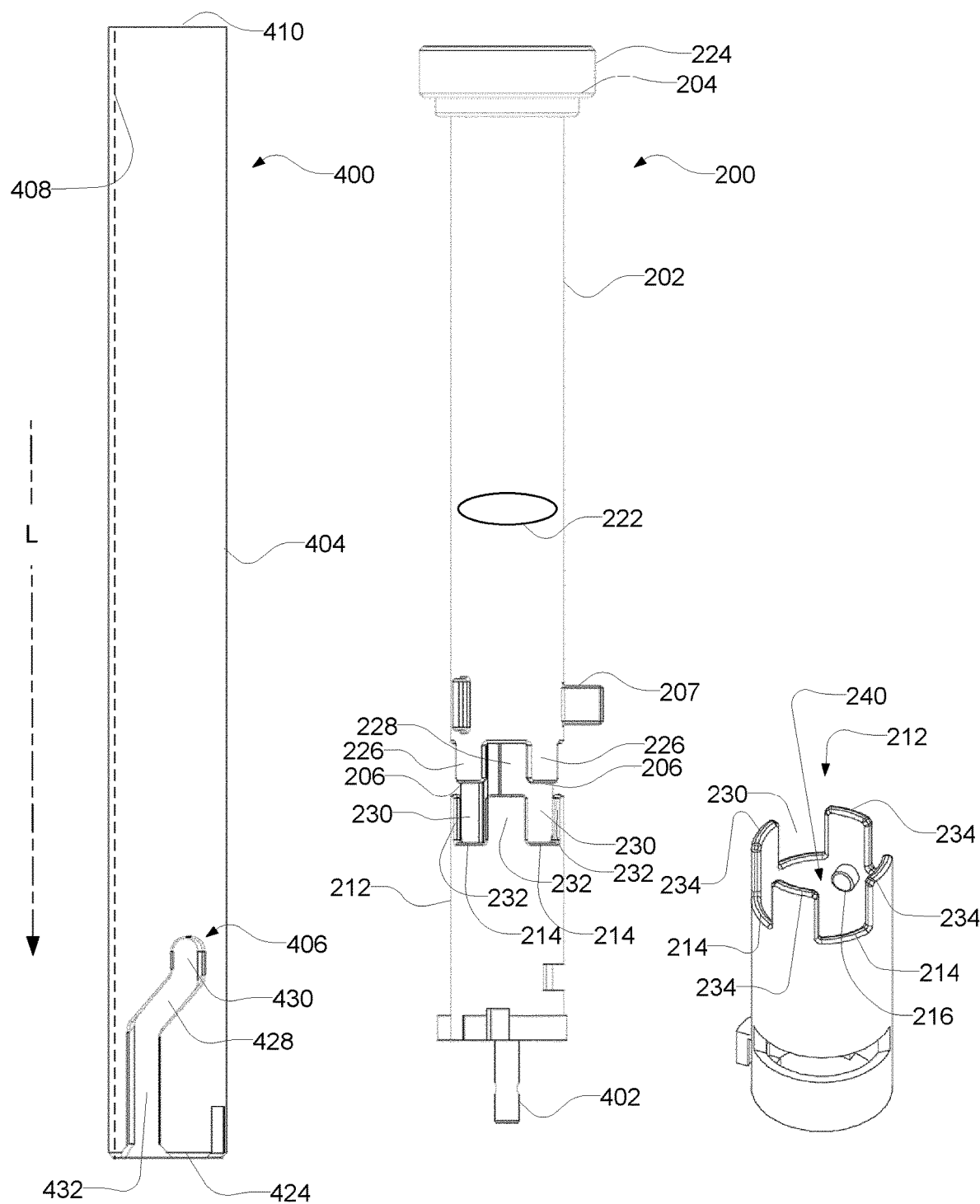
FIG. 11 shows an outer plunger rod.
FIG. 12 shows an ejector.
FIG. 13 shows an ejector lock.

FIG. 11 shows an outer plunger rod. The outer plunger rod 404 is comprised by the plunger 400 and has a plunger rod front end 410 with a dimension that allows it to extend inside the cartridge to move a stopper therein. The outer plunger rod 404 may be moved by an inner plunger rod (not shown) and the inner plunger rod and the outer plunger rod may be coupled by threading such that turning of the inner plunger rod inflicts a longitudinal movement of the outer plunger rod 404. The outer plunger rod 404 may be retaining at an angle about the longitudinal axis by means of a longitudinally extending plunger rod groove 408 in the outer wall of the outer plunger rod.

The outer plunger rod 404 is configured with a plunger rod track 406. The track 406 may extend from the rim of the outer plunger rod at the other end than the plunger rod front end 410. The plunger rod track 406 has at least one track portion 428 that leads an ejector lock guide pin 216 (cf. FIG. 13) from a first angle to a second angle that are angularly spaced apart to turn an ejector lock 212 (cf. FIG. 13) from the first angular position to the second angular position. A second track portion 432 extends from a plunger rod distal rim 424 along the longitudinal axis, L, towards and to connect with the first track portion 428 which is inclined with respect to the longitudinal axis e.g. at an angle of about 45°, e.g. about 30-45°, with respect to the longitudinal axis, L. Thereby the second track portion 432 accommodates the ejector lock guide pin 216 when the outer plunger rod 404 is in a forward position, towards the cartridge receiver opening 301, to expel a medicament by moving the first stopper 708 in the first stopper direction as mentioned above. When the second track portion 432 accommodates the ejector lock guide pin 216, the ejector lock 212 is angularly positioned to prevent the ejector rod 202 from moving backwards. A third track portion 430 connects with the first track portion 428 and continues along the longitudinal axis towards the plunger rod front end 410. Thereby the third track portion 430 accommodates the ejector lock guide pin 216 when the outer plunger rod 404 is in a backward position, opposite the cartridge receiver opening 301, whereat the outer plunger rod 404 is moved backwards, away from the first stopper 708. Thus, the longitudinal position of the outer plunger rod 404 has the dual function of:

- engaging/disengaging with/from the first stopper 708 to expel medicament or being withdrawn from the first stopper 708 to forgo expel of medicament or removing the cartridge assembly 600; and
- locking/unlocking the ejector rod 202 via rotation of the ejector lock 212.

This is explained in greater detail below.

Thus, the outer plunger rod part 404 is configured with a plunger rod track 406 that engages with the ejector lock guide pin 216 and extends from a plunger rod distal rim 424 towards plunger rod front end 410 and thus the cartridge receiver opening 301.

FIG. 12 shows an ejector and an ejector lock. The ejector is generally designated 200 and comprises an ejector rod 202. The ejector lock is configured to engage with the ejector rod by turning to thereby introduce a stop that prevents the ejector rod 202 from moving in the receiving direction.

The ejector rod has an ejector collar 224 arranged about an ejector support face 204, which supports the cartridge at a cartridge back face 716, which may have the form of a rim. The ejector rod 202 has an ejector rod bore 222 to form a longitudinal passage all through the ejector rod 202. The ejector rod bore 222 allows the outer plunger rod 404 to move along the longitudinal axis.

The ejector rod 202 is configured with one or more ejector cut-outs 228 to form one or more ejector cogs 226 between the ejector cut-outs 228. Complementary therewith, the ejector lock 212 is configured with one or more ejector lock cogs 232 between one or more ejector lock cut-outs 230, respectively. The ejector lock 212 is supported e.g. in a bearing that allows the lock to turn or be turned, at least a fraction of a revolution, while preventing a longitudinal movement. The ejector lock 212 may have a flange or a recess that engages with a complementary recess or protrusion, respectively, to maintain the ejector lock 212 in a fixed longitudinal position while allowing it to be turned at least a fraction of a revolution. The ejector cut-outs 228 are also denoted ejector slots 228.

As shown, the ejector lock 212 has an angular position such that the ejector lock cogs 232 align with the ejector cut-outs 228. The ejector rod 202 can thus move in the receiving direction until an end portion 206 of the ejector cogs abuts a bottom portion 214 of the ejector lock cut-outs 230, since the ejector lock cogs 232 and the ejector cogs 226 have substantially the same length. Thus, a bottom portion 214 of the ejector lock cut-outs 230 abuts the end portion 206 of the ejector cogs 226. The end portion 206 of the ejector rod 202 is also denoted an ejector rest portion 206.

When the ejector lock 212 is turned such that ejector cogs 226 align with ejector lock cogs 232, a stop is introduced and the ejector rod 202 is prevented from moving in the receiving direction. The stop is introduced because, in that angular position of the ejector lock 212, the end portion 206 of the ejector rod 202 abuts the ejector lock support portion 234 of the ejector lock 212. The ejector lock support portion 234 of the ejector lock 212 is also denoted an ejector lock support portion 234.

The ejector rod 202 may be prevented from turning, by means of an angle retaining guide 207 when it engages with an angle retaining slot 238 (cf. FIG. 15), wherein the angle retaining slot 238 is arranged on or in the cartridge receiver 300 or a member rigidly coupled to the cartridge receiver 300.

FIG. 13 shows an ejector lock. The ejector lock 212 is shown in greater detail here. It can be seen that the ejector lock 212 is configured with an ejector lock bore 240 accepting at least an end portion of the outer plunger rod 404.

An ejector lock guide pin 216 sits in the ejector lock bore 240 and extends inwardly from a wall thereof.

Figure 14:
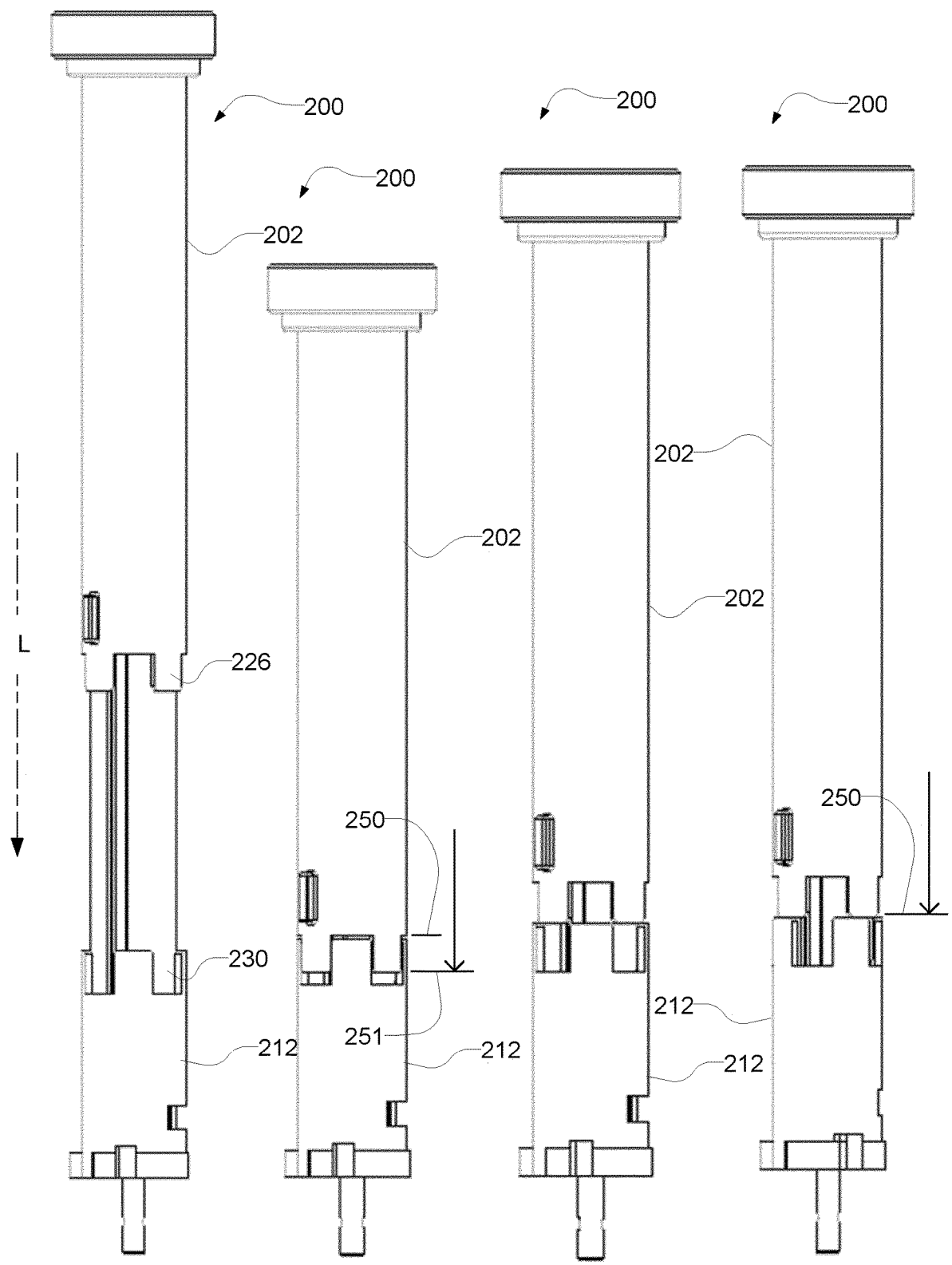
FIG. 14a through 14d shows various positions of the ejector relative to the ejector lock.

FIG. 14a through 14d shows various positions of the ejector relative to the ejector lock. In FIG. 14a the ejector rod 202 is shown in a longitudinal forward extreme position, relative to the ejector lock 212, where it is spring-biased to be when a cartridge assembly is not inserted through the cartridge receiver opening, e.g. as shown in FIG. 1. It can be seen that the ejector cogs 226 are aligned with ejector lock cut-outs 230, although displaced far from each other, such that the stop is disengaged and the ejector rod 202 is thus allowed to move to an extreme position in the receiving direction. Thereby the inbound journey and the outbound journey described in connection with FIG. 8b can take place during insertion or ejection of a cartridge assembly.

In FIG. 14b the ejector rod 202 is shown in a longitudinal backward extreme position e.g. when a cartridge assembly retention member 808 is in contact with the second section 330 of the retention mechanism. This position of the cartridge assembly retention member 808 corresponds to the position L1 or L3 shown in FIG. 8b.

In FIG. 14c the ejector rod 202 is shown in a longitudinal position where the cartridge assembly retention member 808 is in the retention position abutting the bottom of the concave shape of the first guide member 312 of the first section 310. This position of the cartridge assembly retention member 808 corresponds to the position L2 shown in FIG. 8b.

In FIG. 14d the ejector rod 202 is shown in the same longitudinal position as in FIG. 14c, but the ejector lock 212 is turned such that the stop is engaged. In this situation the ejector cogs 226 abuts the ejector lock cogs 232 end-to-end. Thus, an end portion 206 of the ejector cogs 226 abuts the end portion 234 of the ejector lock cogs 232.

Thus, at least both of the length of the ejector rod 202 and the length of the cogs and the cut-outs should be dimensioned to allow the cartridge assembly retention member 808 to travel between position L1 and L2 and L3 and L2.

Thus, the elongated ejector 200 is suspended to move along the longitudinal axis, L, and is enabled to move beyond a stop position 250 (cf. FIG. 14b) at a first angular position of ejector lock 212 and is prevented from moving beyond the stop position 250 by the ejector cogs 226 abutting the ejector lock cogs 232 at a second angular position of the ejector lock 212 (cf. FIG. 14d). At the first angular position of ejector lock, the elongated ejector is enabled to move beyond the stop position, such as further until an extreme position 251 since the ejector cogs enter the ejector lock cut-outs 230 between the ejector lock cogs 232. In some aspects the ejector rod is a substantially cylindrical rod coaxially arranged with the ejector lock, which comprises a substantially cylindrical portion.

Figure 15:
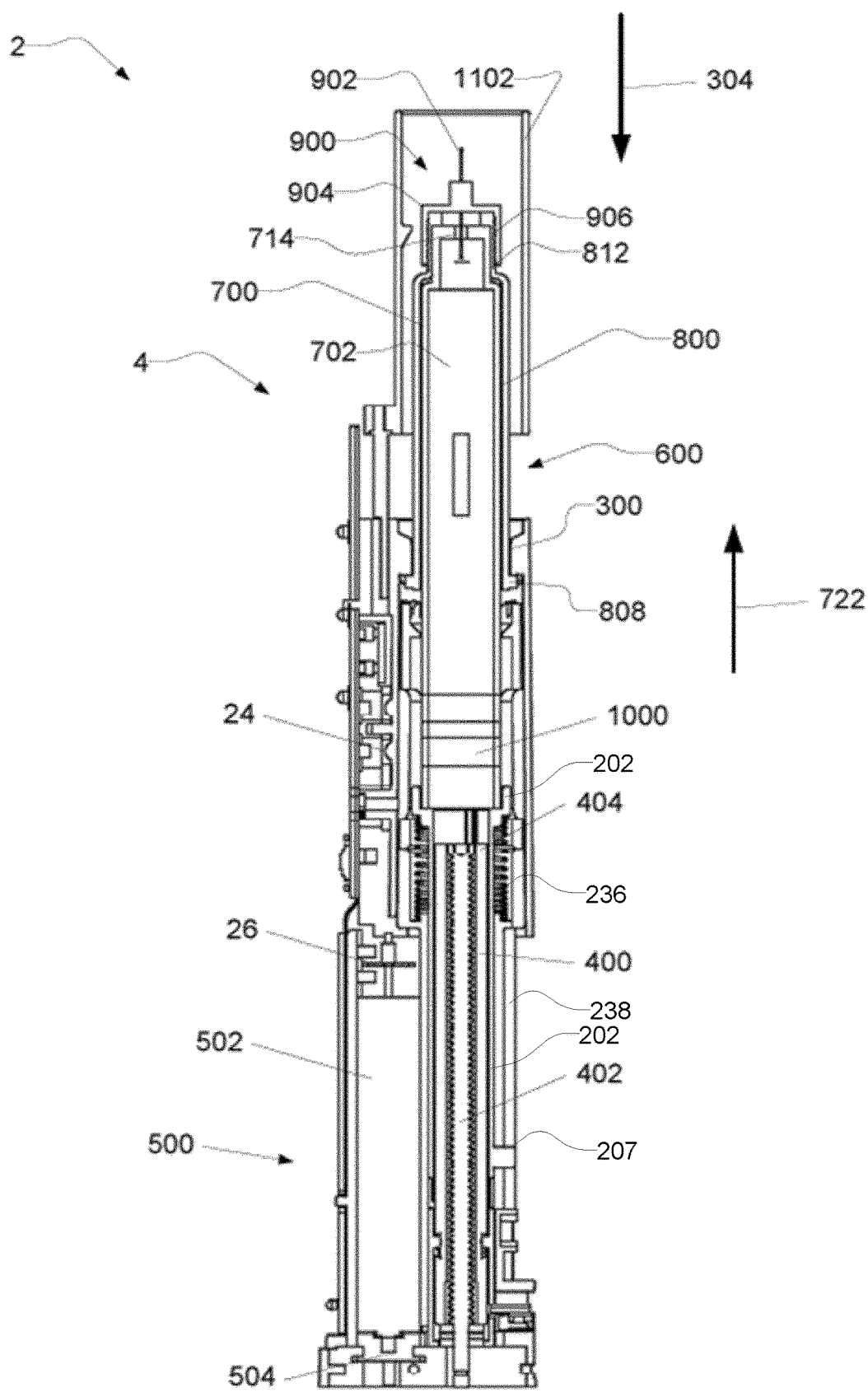
FIG. 15 shows a cross section of an exemplary system comprising an auto injector and a cartridge assembly.

FIG. 15 shows a cross section of an exemplary system comprising an auto injector and a cartridge assembly. The cartridge assembly 600 comprises a cartridge 700 with a cartridge compartment 702, a needle assembly 900, and a cartridge code feature 1000. The cartridge assembly 600 is received in the auto injector 4. The auto injector 4 comprises the ejector rod 202 as described above. The ejector rod 202 is suspended for longitudinal movement and is spring-loaded by an ejector spring 236 which spring-loads the ejector rod 202 in the direction opposite of the receiving direction. Thereby, during insertion of the cartridge assembly 600, the spring force exercised by the ejector spring 236 has to be overcome to insert the cartridge assembly into a position where it is held in a retention position.

The cartridge assembly 600 comprises a cartridge holder 800. The cartridge holder 800 is configured for retention of the cartridge 700 in the cartridge receiver 300 of the auto injector 4. The cartridge holder 800 comprises a cartridge retention member 808. The cartridge retention member 808 engages with the cartridge receiver 300 for reception and retention of the cartridge 700 and the cartridge assembly 600 in the cartridge receiver 300.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700. The cartridge outlet 714 may be blocked by a resilient sealing being penetrated by the needle 902, when the needle assembly 900 is attached to the cartridge 700.

The auto injector 4 comprises a code sensor 24 configured to read the cartridge code feature 1000. When the cartridge assembly 600 is inserted, as shown, the cartridge code feature 1000 is lined up with the code sensor 24.

The auto injector 4 comprises a plunger rod 400. The plunger rod 400 is configured to advance a first stopper of the cartridge 700. The plunger rod 400 comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing of the auto injector. The movement of the plunger rod 400 comprises rotation of the inner plunger rod 402. The rotation of the inner plunger rod 402 results in translational movement of the outer plunger rod 404, due to the outer plunger rod 404 being rotationally restricted. The outer plunger rod 404, when moved translationally in the first stopper direction 722, is configured to abut the first stopper of the cartridge 700, and to move the first stopper in the first stopper direction 722.

The drive module 500 is coupled to actuate the plunger rod 400. The drive module 500 is electrically connected to a battery for receiving electrical power. The drive module 500 comprises a motor 502, such as an electro-mechanical motor, such as a DC motor. The drive module 500 comprises a transmission 504 for coupling the motor 502 to the inner plunger rod 402 of the plunger rod 400.

The auto injector 4 comprises an ejection sensor 26, such as a plunger rod position sensor. The ejection sensor 26 is configured to detect the position of the plunger rod 400. In the illustrated example, the ejection sensor 26 comprises a tachometer configured to count/detect the revolutions of the motor 502. Thus, the position of the plunger rod 400 may be determined based on the count of revolutions of the motor 502. The ejection sensor 26 may, based on the detection of the position of the plunger rod 400, detect the expelling of medicament and/or air in the cartridge compartment. The position of the plunger rod 400 may be indicative of the position of the first stopper of the cartridge 700, e.g. the most advanced position of the plunger rod 400 during reception of the cartridge 700 may be indicative of the position of the first stopper of the cartridge 700.

FIGS. 16a-d show cross sections of a portion of an exemplary system comprising an auto injector and a cartridge assembly. The auto injector 4 comprises a cartridge receiver 300 configured for receiving and retaining a cartridge. The auto injector 4 comprises a contact member 1102. The contact member 1102 may be movable between an extended contact member position and a retracted contact member position. The contact member 1102 comprises a contact member protruding part 1112. The contact member protruding part 1112 is configured to move with the contact member 1102. The contact member 1102 may be biased, e.g. by a contact member spring (not shown), towards the extended contact member position.

The contact member comprises a needle cover engagement member 1114. The needle cover engagement member 1114 is configured to abut a needle cover abutment face, e.g. of a needle cover positioned on the cartridge inserted into the cartridge receiver 300.

The auto injector 4 comprises a contact member sensor 1104 configured to detect a position of the contact member 1102. The contact member sensor 1104 comprises a first contact member sensor 1130 and a second contact member sensor 1132. The first contact member sensor 1130 and the second contact member sensor 1132 may be optical sensors. The contact member sensor 1104 detects the position of the contact member 1102 by the contact member protruding part 1112 covering the first contact member sensor 1130 when the contact member 1102 is in a first contact member position, and the contact member protruding part 1112 covering the second contact member sensor 1110 when the contact member 1102 is in a second contact member position.

The first contact member position may be detected by the first contact member sensor 1130 being covered and the second contact member sensor 1132 being covered. The second contact member position may be detected by the first contact member sensor 1130 not being covered and the second contact member sensor 1132 being covered. The extended contact member position may be detected by the first contact member sensor 1130 not being covered and the second contact member sensor 1132 not being covered.

Figure 16:
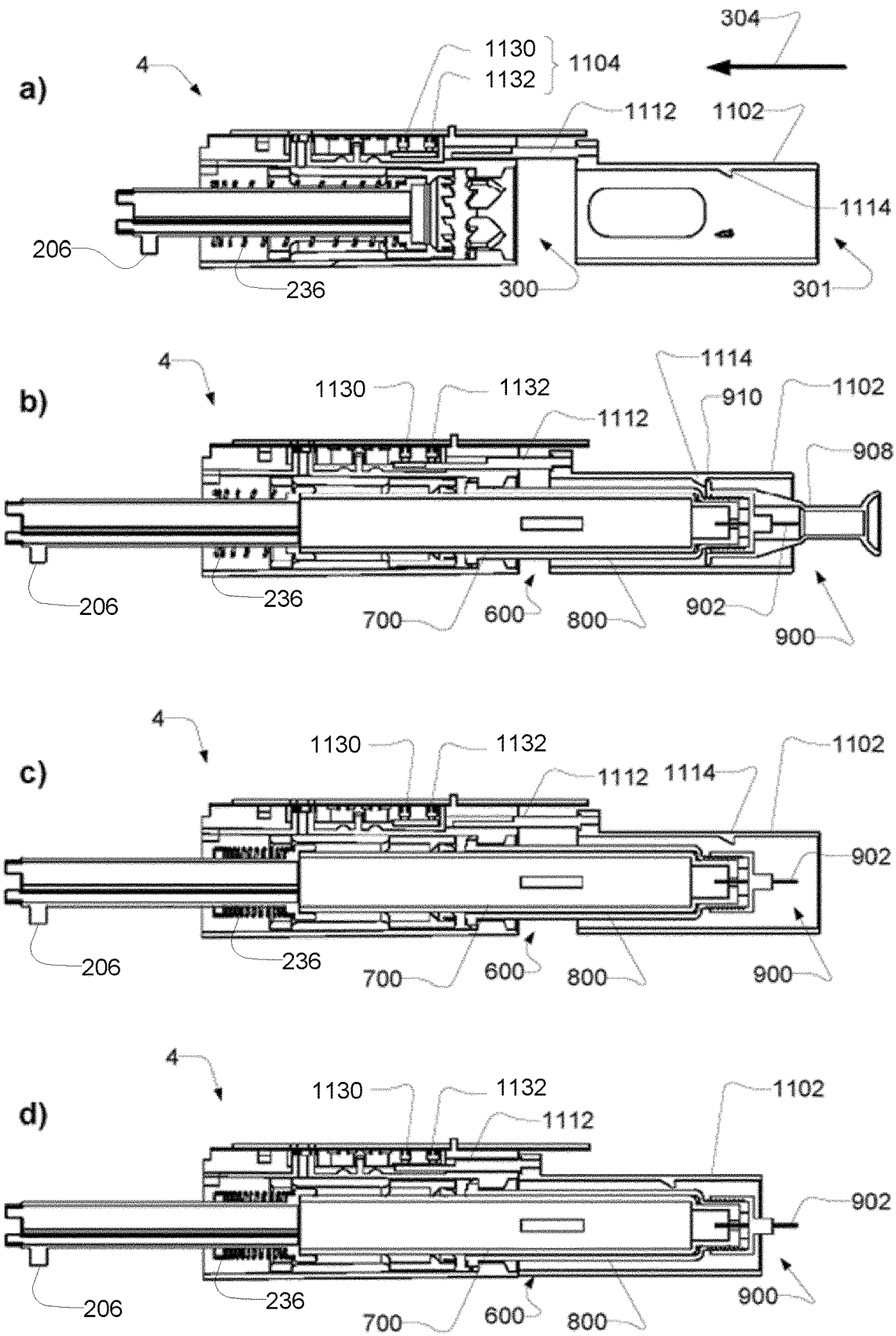
FIGS. 16a-d show cross sections of a portion of an exemplary system comprising an auto injector and a cartridge assembly.

FIG. 16a schematically illustrates the auto injector 4 with no received cartridge and/or cartridge assembly. The contact member 1102 is in the extended contact member position. A cartridge may be inserted into the cartridge receiver 300 in the cartridge receiving direction 304 through the contact member 1102 defining a cartridge receiver opening 301.

FIG. 16b schematically illustrates the auto injector 4 with a cartridge assembly 600 received. The cartridge assembly comprises a cartridge 700, a cartridge holder 800 and a needle assembly 900. The needle assembly comprises a needle 902 and a needle cover 908. The needle cover has a needle cover abutment face 910. The needle cover abutment face 910 engages the needle cover engagement member 1114 of the contact member 1102. The contact member 1102 is in the second contact member position, e.g. caused by the presence of the needle cover 908 and the abutment of the needle cover abutment face 910 on the needle cover engagement member 1114. The contact member protruding part 1112 covers the second contact member sensor 1132. The contact member protruding part 1112 does not cover the first contact member sensor 1130.

FIG. 16c schematically illustrates the auto injector 4 with a cartridge assembly 600 received. Compared to FIG. 6b, the needle cover 908 has been removed. The contact member 1102 is in the extended contact member position. The contact member 1102 is allowed to be moved to the extended contact member position since the needle cover abutment face 910 does not about the needle cover engagement member 1114. The contact member protruding part 1112 has moved with the contact member 1102. The contact member protruding part 1112 does not cover the second contact member sensor 1132. The contact member protruding part 1112 does not cover the first contact member sensor 1130.

FIG. 16d schematically illustrates the auto injector 4 with a cartridge assembly 600 received. The contact member 1102 is in the first contact member position. The first contact member position may be the retracted contact member position, or close to the retracted contact member position. The contact member 1102 may have been moved to the first contact member position by the contact member 1102 being pressed against an injection site, thereby inserting the needle 902 into the injection site. The contact member protruding part 1112 has moved with the contact member 1102. The contact member protruding part 1112 covers the first contact member sensor 1130.

The contact member protruding part 1112 covers the second contact member sensor 1132.

Figures 17A, 17B:
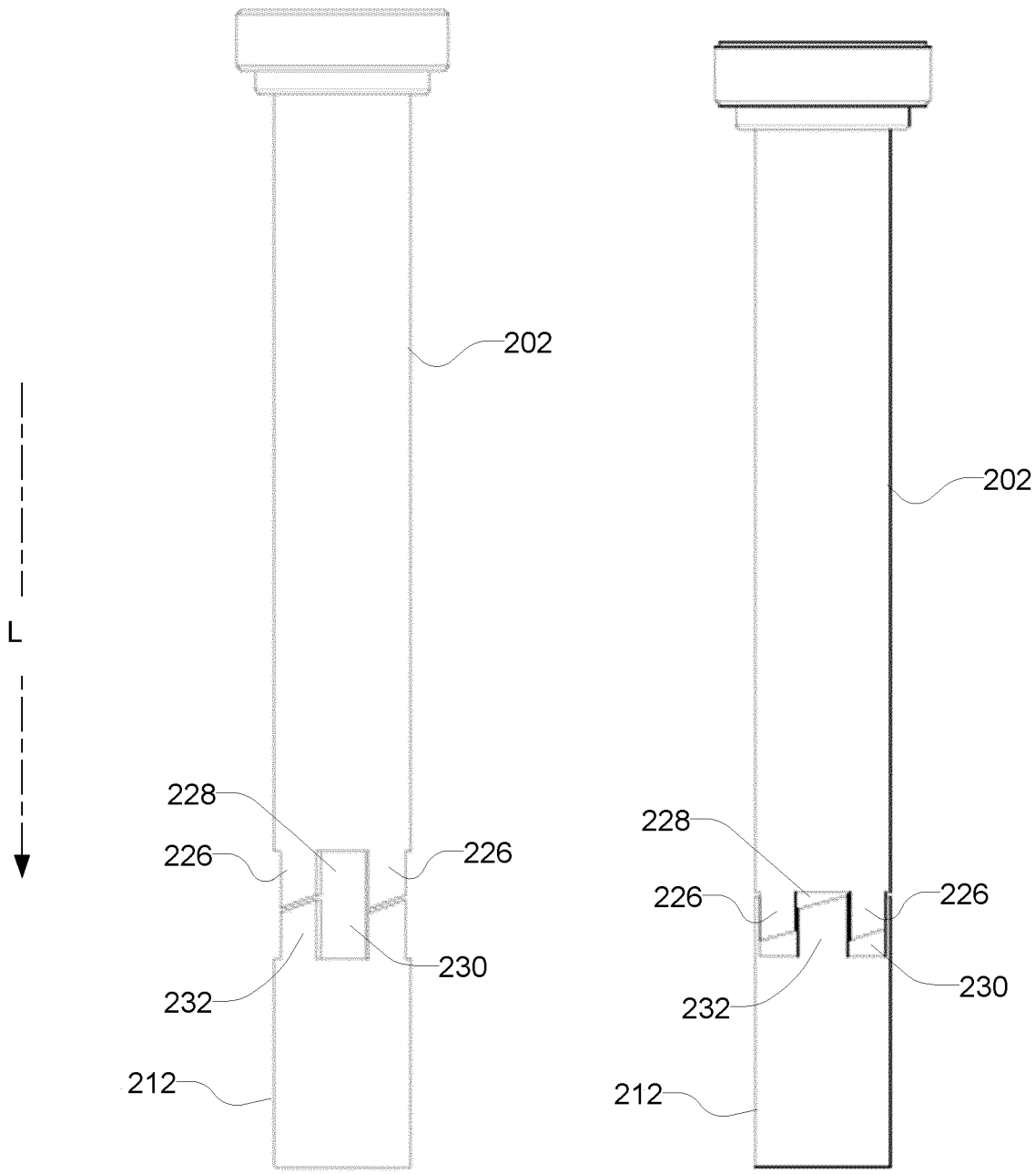
FIG. 17a-b show shows various positions of the ejector relative to the ejector lock in an embodiment where the cogs have inclined faces.

FIG. 17a-b shows various positions of the ejector relative to the ejector lock in an embodiment where the cogs have inclined faces. In FIG. 17a the ejector rod 202 and the ejector lock 212 are in a mutual position where the stop is engaged. However, it can be seen that the ejector lock cogs 232 and the ejector cogs 226 have inclined end portions that abuts one another. Therefore, a further turning of the ejector lock 212 by a few degrees or a fraction of a degree may move the ejector 200 in the direction opposite of the receiving direction to displace it up to and tightly against the cartridge or cartridge assembly. Thereby, it is possible to reduce or eliminate clearances that would otherwise allow the cartridge to move slightly e.g. by as little as a fraction of a millimetre, but that could cause an inaccurate dose being expelled. The amount of tightening force may be controlled e.g. by monitoring current drawn by a motor coupled to drive the ejector lock.

In FIG. 17b the ejector 200 and the ejector lock 212 are in a mutual position where the stop is disengaged. Bottom portions of the ejector cut-outs 228 and/or the ejector lock cut-outs 230 may be inclined by the same angle as the end portions of the cogs to match the cogs or, as shown, have a substantially flat bottom portion, substantially orthogonal to the longitudinal axis.

As a first item the auto injector may comprise an elongated ejector (200) that is configured with: an ejector support face (204) for supporting the cartridge or cartridge assembly (600), a longitudinal ejector slot (228) extending towards the ejector support face (204) from an ejector rest portion (206); wherein the elongated ejector (200) is suspended to move along the longitudinal direction and is spring-loaded in the direction opposite of the receiving direction; and an ejector lock (212) supported for turning at least a fraction of a revolution and maintained in a longitudinal position relative to the housing (6); wherein the ejector lock (212) has a ejector lock support portion (214) that is configured to align with and slide along the longitudinal ejector slot (228) at a first angle and to be brought to align with the ejector rest portion (206) at a second angle. The ejector slots 228 are also denoted ejector cut-outs 228. The ejector rest portion 206 is also denoted an end portion 206 of the ejector rod 202.

As a second item, in accordance with the first item, the ejector (200) may comprise an ejector rod (202) with an ejector support face (204); wherein the ejector rod (202) has an ejector rod bore (222) to form a longitudinal passage, and wherein the ejector support face (204) is arranged at one end of the ejector rod (202) and has a disc shape or an annular shape.

As a third item, in accordance with the first item or second item, the ejector rod (202) comprises an ejector collar (224) arranged about the ejector support face (204).

As a fourth item, in accordance with any of the above items, the ejector (200) comprises an ejector rod (202) configured with one or more ejector cut-outs (228) to form one or more ejector cogs (226) between the ejector cut-outs (228); and wherein the ejector lock (212) is configured with one or more ejector lock cogs (232) between one or more ejector lock cut-outs (230), respectively.

As a fifth item, in accordance with the fourth item, one or more of the cut-outs (230;228) and the cogs (232;226) have a substantially rectangular shape.

As a sixth item, in accordance with the fourth item, the one or more cut-outs (230;228) and the one or more cogs (232;226) comprises a portion that is inclined relative to the longitudinal axis and relative to an axis orthogonal to the longitudinal axis.

As a seventh item, in accordance with the fourth item, ejector cogs (226) and lock cogs (232) comprise an end portion that is inclined relative to the longitudinal axis at an angle of less than 40 degrees or less than 30 degrees or less than 20 degrees relative to the orthogonal of the longitudinal axis.

As an eight item, in accordance with the fourth item, the ejector (200) comprises an ejector rod (202) configured with a substantially cylindrical portion with one or more chamfers about the longitudinal axis to form a rotational asymmetric end portion; and wherein the ejector lock (212) is configured with one or more complementary chamfer cuts to form a complementary rotational asymmetric end portion.

As a ninth item, in accordance with any one of the above items, the auto injector comprises a plunger rod (400); wherein the ejector (200) comprises an ejector rod (202) which is spring-loaded by a spring ejector member (236); wherein the plunger rod (400) and the bore are configured for longitudinal relative movement.

As a tenth item, in accordance with the ninth item, the plunger rod (400) comprises an inner plunger rod part (402) and an outer plunger rod part (404); wherein the inner plunger rod part (402) and the outer plunger rod part (404) are coupled by a thread; wherein the inner plunger part (402) is retained in a bearing allowing rotation of the inner plunger part (402) while preventing a longitudinal movement; and wherein the outer plunger rod part (404) is retained in an angular position relative to the housing (6).

As an eleventh item, in accordance with the tenth item, the auto injector comprises an angle retaining slot (238) and an angle retaining guide (207) configured to engage with each other and arranged on or in the cartridge receiver (300) or a member rigidly coupled to the cartridge receiver (300) and at the ejector rod (202).

As a twelfth item, in accordance with any one of the above items, the ejector lock (212) comprises an ejector lock guide pin (216) configured to engage with a plunger rod track (432) provided in the plunger rod (400), such that longitudinal movement of the plunger rod (400), at least over a predefined range, inflicts a turning of the ejector lock (212) about the longitudinal axis (L).

As an thirteenth item, in accordance with the twelfth item, movement of the plunger rod (400) in the receiving direction, at least over a range of longitudinal positions, inflicts a turning of the ejector lock (212) to the first angular position.

As a fourteenth item, in accordance with the twelfth item, the ejector lock (212) is configured with an ejector lock bore (240) to accept at least an end portion of the outer plunger rod (404) and an ejector lock guide pin (216) that extends inwardly from a wall of the ejector lock bore (240); wherein the outer plunger rod (404) is configured with a plunger rod track (406) that engages with the ejector lock guide pin (216) and extends from a plunger rod distal rim (424) towards the cartridge receiver opening (301); wherein the plunger rod track (406) has at least one track portion that leads the ejector lock guide pin (216) from a first angle to a second angle that are angularly spaced apart to turn the ejector lock (212) from the first angular position to the second angular position.

As a fifteenth item, in accordance with the twelfth item, the plunger rod track (406) is configured as a recess that extends from the plunger rod distal rim (424) of the outer plunger rod (404).

As a sixteenth item, in accordance with any one of the above items, the ejector lock (212) is coupled to a resilient member that biases the ejector lock towards the second angular position.

As a seventeenth item, in accordance with any one of the above items, the auto injector comprises a drive module with a motor and one or more of transmission and gearing to couple the motor to the inner plunger rod.

As an eight item, there is provided an auto injector (4) for administering injection of a medicament from a cartridge (700) containing the medicament, the auto injector comprising: a housing (6); and a cartridge receiver (300) with a cartridge receiver compartment (302) configured to receive a cartridge assembly (600) with at least one cartridge retention member (808) when inserted through a cartridge receiver opening (301) along a longitudinal axis; and an ejector (200) configured to support the cartridge assembly (600) by being suspended to move along the longitudinal direction and being spring-loaded in the direction opposite of the receiving direction; wherein the cartridge receiver compartment (302) has a first section (310), at a first distance from the cartridge receiver opening (301), with inwardly extending first guide members (312) that extends over first guide member angles (314) and are spaced apart to form a passage (316) at passage angles (318) between the inward first guide members (312); wherein the inward first guide members (312) form a first bore (320) accepting the cartridge assembly (600) when inserted through the cartridge receiver opening (301); wherein the cartridge receiver compartment (302) has a second section (330) with an annular shape, at a second distance from the cartridge receiver opening (301), and with second guide members (322) with first faces (324) that are inclined about a radial axis to the longitudinal axis and angularly arranged to extend at least partly over passage angles (318) and first guide member angles (314).

As a ninth item, in accordance with the above item eight there is provided an auto injector, wherein one or more of the first guide members (312) has/have a face that faces away from the cartridge receiver opening (302) and forms a concave shape with a slope portion (334), at slope angles (336), leading towards a retention portion (328) at or about a bottom portion of the concave shape.

As a tenth item, in accordance with the above item eight or nine there is provided an auto injector, wherein the second guide member (322) has second faces (326) that are inclined about a radial axis to the longitudinal axis and are arranged alternately with the first faces (324); wherein the first faces (324) and the second faces (326) are inclined towards greater distance from the cartridge receiver opening (301) in a direction of rotation being either a clockwise or anticlockwise direction; wherein the first faces (324) and the second faces (326) are separated by first riser portions (340); and wherein the first riser portions (340) are angularly positioned at or within the first guide member angles (314).

Other aspects of the items above are set out in the claims and in the present specification.

The invention claimed is:

1. An auto injector for administering an injection of a medicament from a cartridge containing the medicament, the auto injector comprising:
   a housing; and
   a cartridge receiver with a cartridge receiver compartment configured to receive a cartridge assembly with at least one cartridge retention member when inserted through a cartridge receiver opening along a longitudinal axis; and
   an ejector configured to support the cartridge assembly by being suspended to move along the longitudinal direction and being spring-loaded in the direction opposite of the receiving direction;
   wherein the cartridge receiver compartment has a first section, at a first distance from the cartridge receiver opening, with inwardly extending first guide members that extend over first guide member angles and are spaced apart to form a passage at passage angles between the inward first guide members; wherein the inward first guide members form a first bore accepting the cartridge assembly when inserted through the cartridge receiver opening;
   wherein one or more of the first guide members has a face that faces away from the cartridge receiver opening and forms a concave shape with a slope portion, at slope angles, leading towards a retention portion at or about a bottom portion of the concave shape;
   wherein the cartridge receiver compartment has a second section with an annular shape, at a second distance from the cartridge receiver opening, and with second guide members with first faces that are inclined about a radial axis to the longitudinal axis and angularly arranged to extend at least partly over passage angles and first guide member angles;
   wherein the second guide member has second faces that are inclined about a radial axis to the longitudinal axis and are arranged alternately with the first faces;
   wherein the first faces and the second faces are inclined towards a greater distance from the cartridge receiver opening in a direction of rotation being either a clockwise or anticlockwise direction;
   wherein the first faces and the second faces are separated by first riser portions; and
   wherein the first riser portions are angularly positioned at or within the first guide member angles.

2. The auto injector according to claim 1, wherein the first guide members have a first guide face that faces the cartridge receiver opening and forms a convex pointing shape with an apex directed towards the cartridge receiver opening.

3. The auto injector according to claim 1, wherein the first section and the second section maintains a fixed angular position with respect to each other.

4. The auto injector according to claim 1, wherein the first section and the second section are integrally formed with the cartridge receiver to form a single piece.

5. The auto injector according to claim 3,
   wherein one or more first riser portions are angularly arranged at slope angles; and
   wherein one or more first riser portions are angularly arranged between the retention angle and a centre of passage angles in a direction of rotation being either a clockwise or anticlockwise direction.

6. The auto injector according to claim 4, wherein one or more of the first faces and the second faces are divided into sections separated by a second riser portion.

7. The auto injector according to claim 5, wherein a first guiding member has an eject face that is inclined towards the cartridge receiver opening at angles beyond the retention angle in a direction of rotation being either a clockwise or anticlockwise direction.

8. The auto injector according to claim 1, wherein the second guide members are configured as a first set of steps with treads that are inclined about the radial axis and a second set of steps with treads that are inclined about the radial axis;
   wherein the treads of the first and second steps are inclined towards greater distance from the cartridge receiver opening for a clockwise or anticlockwise direction of rotation;
   wherein the treads of the first set of steps are arranged more proximal to the cartridge receiver opening than the treads of the second set of steps; and
   wherein the first set of steps are alternately arranged with the second set of steps; with riser portions between the steps, forming an annular member comprised by the second section.

9. The auto injector according to claim 3, wherein the one or more first guide members and the second guide members are configured and angularly aligned such that:
   upon insertion, the cartridge retention member passes the passage in a longitudinal direction, lands on a first section of the first face, by rotation follows the first face out over a second riser portion to a second section, and
   upon ease of an insertion force, the cartridge retention member travels to the retention portion via the slope portion.

10. The auto injector according to claim 5, wherein the one or more first guide members and the second guide members are configured and angularly aligned such that:
    upon release, the cartridge retention member leaves the retention portion and lands on the first section of the second face, by rotation follows the second face out over a second riser portion to a second section; and
    upon ease of a force, the cartridge retention member travels to the eject face, wherefrom a the cartridge retention member is guided towards the cartridge receiver opening via a passage.

11. The auto injector according to claim 1, wherein the ejector comprises an ejector lock that is operative by one or more of rotation, translational movement or axial movement to move to a position where movement of the ejector is restricted in the direction of insertion.

12. The auto injector according to claim 1, wherein the elongated ejector is configured with:
    an ejector support face for supporting the cartridge or cartridge assembly, a longitudinal ejector slot extending towards the ejector support face from an ejector rest portion; and
    an ejector lock supported for turning at least a fraction of a revolution and maintained in a fixed longitudinal position relative to the housing; wherein the ejector lock has a ejector lock support portion that is configured to align with and slide along the longitudinal ejector slot at a first angle and to be brought to align with the ejector rest portion at a second angle.

13. The auto injector according to claim 1, wherein the ejector comprises an ejector rod configured with one or more ejector cut-outs to form one or more ejector cogs between the ejector cut-outs; and wherein the ejector lock is configured with one or more ejector lock cogs between one or more ejector lock cut-outs, respectively.

14. The auto injector according to claim 13, wherein one or more of the cut-outs and the cogs have a substantially rectangular shape.

15. The auto injector according to claim 1, comprising a plunger rod operative by movement along the longitudinal axis to exercise a pressing force on a cartridge accommodated in the cartridge assembly.

16. The auto injector according to claim 15, wherein the plunger rod is accommodated in the ejector to be longitudinally displaceable.

17. The auto injector according to claim 15, wherein the ejector lock comprises an ejector lock guide pin configured to engage with a plunger rod track provided in the plunger rod, such that longitudinal movement of the plunger rod, at least over a predefined range, inflicts a turning of the ejector lock about the longitudinal axis.

18. The auto injector according to claim 17, wherein the plunger rod track comprises at least one track portion that guides the ejector lock guide pin from a first angle to a second to turn an ejector lock from the first angular position to the second angular position.

19. The auto injector according to claim 1 comprising an operational module configured to:
 engage the plunger rod to move along the longitudinal axis to exercise a pressing force on a cartridge accommodated in the cartridge assembly; and
 engage an ejector lock by one or more of rotation, translational movement or axial movement to move to a position where movement of the ejector is restricted in the direction of insertion.

* * * * *